US009482668B2

(12) United States Patent
Anderson et al.

(10) Patent No.: US 9,482,668 B2
(45) Date of Patent: Nov. 1, 2016

(54) METHODS AND SYSTEMS FOR THE DETECTION OF BACTERIA

(71) Applicant: Laboratory Corporation of America Holdings, Burlington, NC (US)

(72) Inventors: Dwight Lyman Anderson, Minneapolis, MN (US); Andrew J. Conrad, Malibu, CA (US); Stephen Erickson, White Bear Township, MN (US); Jose S. Gil, Winnetka, CA (US); Ben Barrett Hopkins, Los Angeles, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 0 days.

(21) Appl. No.: 13/773,339

(22) Filed: Feb. 21, 2013

(65) Prior Publication Data

US 2013/0216997 A1    Aug. 22, 2013

Related U.S. Application Data

(60) Provisional application No. 61/601,231, filed on Feb. 21, 2012.

(51) Int. Cl.
*C12Q 1/70* (2006.01)
*G01N 33/569* (2006.01)
*G01N 33/58* (2006.01)

(52) U.S. Cl.
CPC ........... *G01N 33/56911* (2013.01); *C12Q 1/70* (2013.01); *G01N 33/569* (2013.01); *G01N 33/581* (2013.01)

(58) Field of Classification Search
CPC .... C12Q 1/04; C12Q 1/70; C12Q 2561/113; C12Q 1/025; C12Q 1/045; G01N 33/56911; G01N 33/54326; G01N 33/569; G01N 33/581; G01N 33/554; A61K 35/76; C12N 2795/00032; C12N 7/00; C12N 2795/00
See application file for complete search history.

(56) References Cited

U.S. PATENT DOCUMENTS

| | | | |
|---|---|---|---|
| 5,824,468 A * | 10/1998 | Scherer et al. | 435/5 |
| 5,837,465 A | 11/1998 | Squirrell et al. | |
| 7,252,996 B2 * | 8/2007 | Boccaccio et al. | 435/377 |
| 8,557,970 B2 | 10/2013 | Encell et al. | |
| 2004/0137430 A1 | 7/2004 | Anderson et al. | |
| 2005/0003346 A1 * | 1/2005 | Voorhees et al. | 435/5 |
| 2009/0246752 A1 | 10/2009 | Voorhees et al. | |
| 2010/0291541 A1 | 11/2010 | Evoy et al. | |
| 2011/0201013 A1 | 8/2011 | Moore | |
| 2013/0122549 A1 | 5/2013 | Lu et al. | |
| 2013/0216997 A1 | 8/2013 | Anderson et al. | |

FOREIGN PATENT DOCUMENTS

WO    WO 99/45396    9/1999

OTHER PUBLICATIONS

He, Y. et al., Monoclonal antibodies for detection of the H7 antigen of *Escherichia coli*, Appl. Environ Microbiol., 1996, 62(9):3325-32.
Inouye, S. et al., Overexpression, purification and characterization of the catalytic component of *Oplophorus* luciferase in the deep-sea shrimp, *Oplophorus gracilirostris*. Protein Expr. Purif., 2007, 56(2):261-8.
Kodikara, C. et al., Near on-line detection of enteric bacteria using lux recombinant bacteriophage, FEMS Microbiol. Lett., 1991, 67(3):261-5.
Lu, T. et al., Advancing bacteriophage-based microbial diagnostics with synthetic biology, Trends Biotechnol., 2013, 31(6):325-7.
Rees C., The Use of Phage of Diagnostic Systems, Division of Food Sciences, School of Biosciences, University of Nottingham, Sutton Bonington Campus Loughborough, Leicestershire LE12 5RD, UK; The Bacteriophages, 2nd edition (2006) Richard Calendar—Oxford University Press.
Schofield, D. et al., Phage-based platforms for the clinical detection of human bacterial pathogens, Bacteriophage, 2012, 2(2):105-283.
Bague, J., Detection of Recombinant Human Erythropoietin and Analogues through Immunorecognition and N-Giycolyi-Neuraminic Acid Identification, Doctoral Thesis Pompeu Fabra University, Department of Experimental and Health Sciences, 2011. Retrieved from http://www.tesisenred.net/bitstream/handle/10803/31969/tjm.pdf?sequence=1 as available via the Internet and printed Mar. 27, 2013.
Patent Cooperation Treaty, International Search Report and Written Opinion, International Application No. PCT/US13/27155, dated May 6, 2013.
European Patent Office, Extended European Search Report, European Application No. 13751965 dated Sep. 30, 2015.
Edgar, R. et al., High-sensitivity bacterial detection using biotin-tagged phage and quantum-dot nanocomplexes, Proc. Natl. Acad. Sci. USA, 2006, 103(13):4841-5. Epub Mar. 20, 2006.
Goodridge, L. et al., Reporter bacteriophage assays as a means to detect foodborne pathogenic bacteria, Food research International, 2002, 35:863-870.
Hagens, S. et al., Reporter bacteriophage A511::celB transduces a hyperthermostable glycosidase from Pyrococcus furiosus for rapid and simple detection of viable Listeria cells, Bacteriophage, 2011, 1(3):143-151. Epub May 1, 2011.
Loessner, M. et al., Evaluation of luciferase reporter bacteriophage A511::luxAB for detection of Listeria monocytogenes in contaminated foods, Appl. Environ. Microbiol., 1997, 63(8):2961-5.
Loessner, M. et al., Construction of luciferase reporter bacteriophage A511::luxAB for rapid and sensitive detection of viable Listeria cells, Appl. Environ. Microbiol., 1996, 62(4):1133-40.

(Continued)

*Primary Examiner* — Nicole Kinsey White
(74) *Attorney, Agent, or Firm* — Kilpatrick Townsend & Stockton LLP

(57) ABSTRACT

Disclosed are methods and systems for the isolation and detection of microbes from a sample. The use of binding agents for isolation of a microbe of interest from a sample are described. In certain embodiments, the methods use ribosome-based and/or bacteriophage-based amplification of the signal in detection of bacteria and other microorganisms. For example, embodiments of the present invention can achieve total amplification of at least 10,000 from a single infected cell.

17 Claims, 23 Drawing Sheets

(56) References Cited

OTHER PUBLICATIONS

Noguera, P. et al., Carbon nanoparticles in lateral flow methods to detect genes encoding virulence factors of Shiga toxin-producing, Anal Bioanal. Chem., 2011, 399(2): 831-838.

Rees, C. et al., Chapter 14—The use of phage detection, antibiotic sensitivity testing and enumeration, In: Understanding Tuberculosis—Global Experiences and Innovative Approaches to the Diagnosis, 2012, Intech, Edited by Dr. Pere-Joan Cardona.

Smietana, M. et al., Detection of bacteria using bacteriophages as recognition elements immobilized on long-period fiber gratings, Opt Express., 2011, 19(9):7971-8.

Wu, L. et al., Trace detection of specific viable bacteria using tetracysteine-tagged bacteriophages, Anal Chem. 2014, 86(1):907-12. Epub Dec. 10, 2013.

Ulitzur, N. et al., New rapid and simple methods for detection of bacteria and determination of their antibiotic susceptibility by using phage mutants, Appl. Environ. Microbiol., 2006, 72(12):7455-7459.

Patent Cooperation Treaty, International Search Report and Written Opinion, International Application No. PCT/US2015/016415, dated Jun. 22, 2015.

State Intellectual Property Office of the Peoples Republic of China, Notification of the First Office Action, Application No. 201380019483, dated Jul. 7, 2015.

* cited by examiner

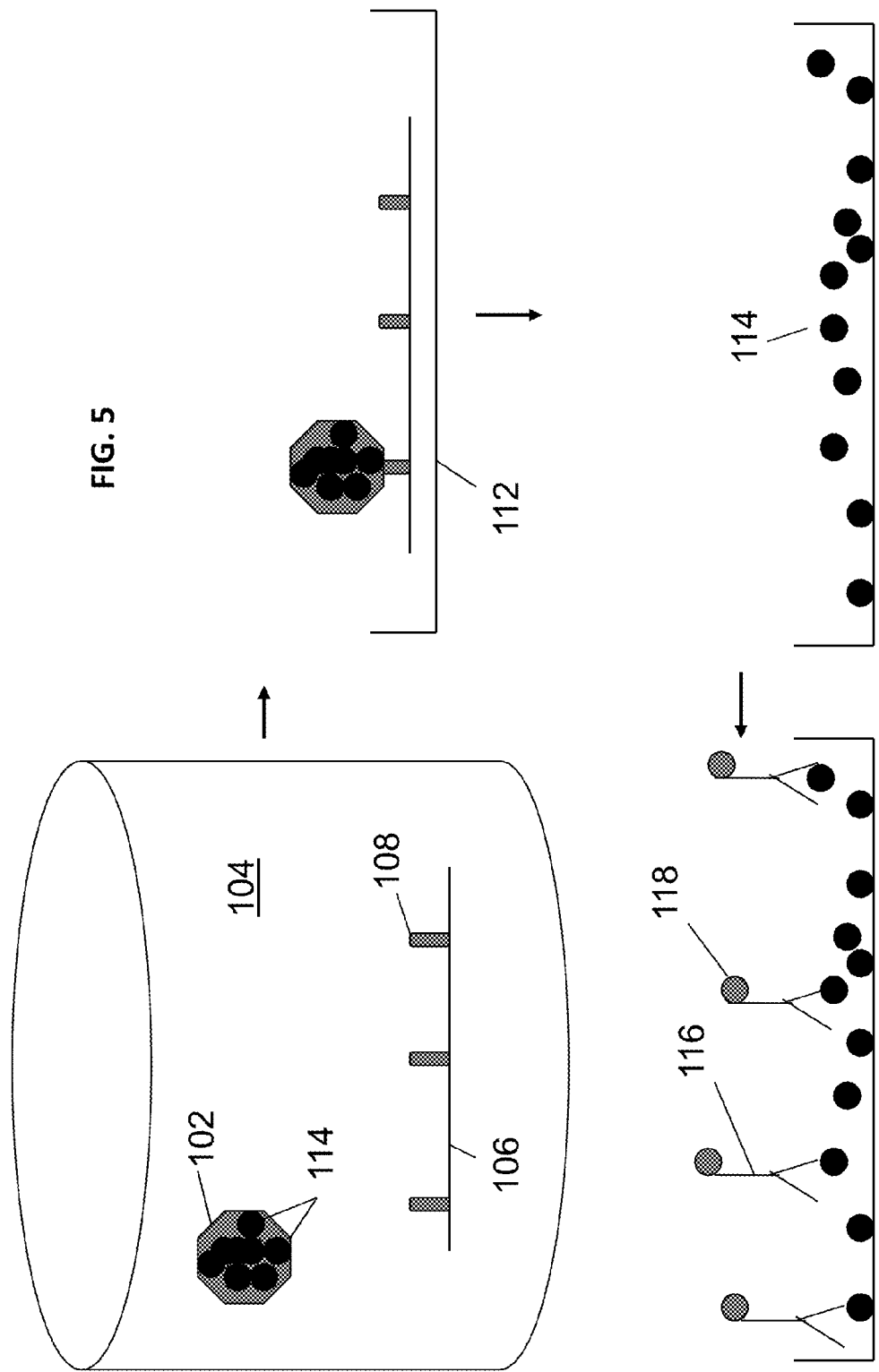

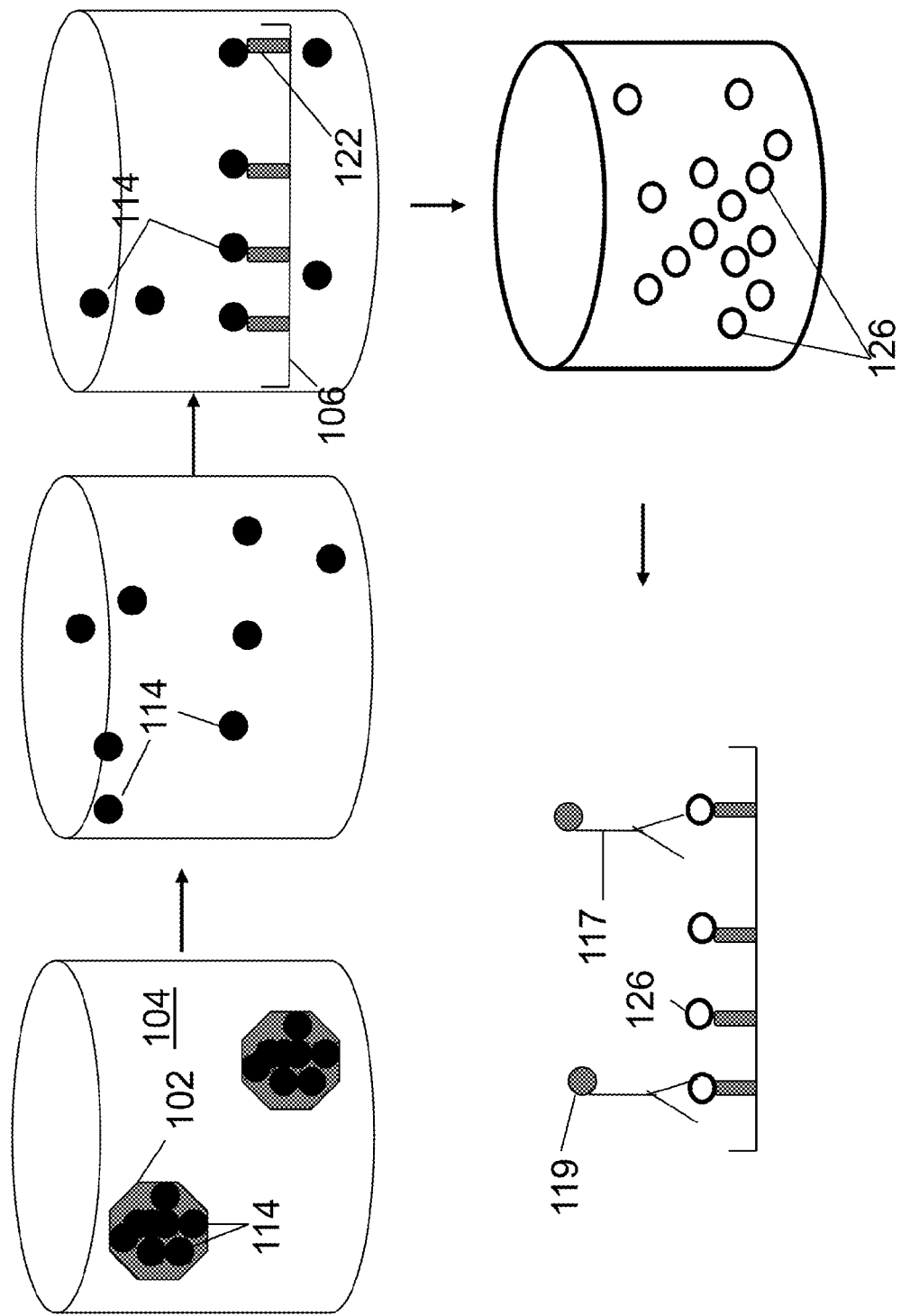

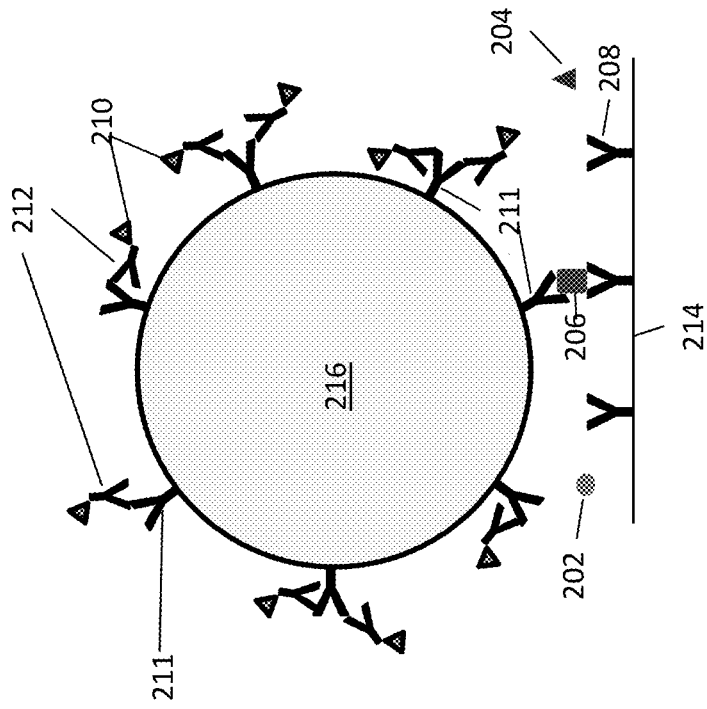
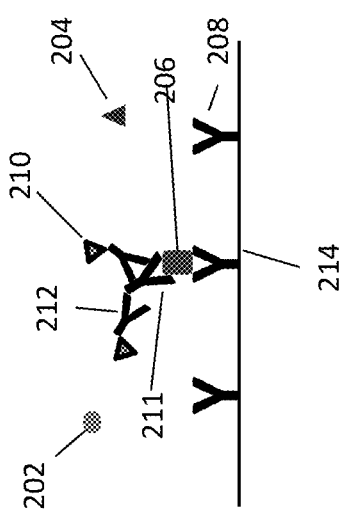
FIG. 7B
FIG. 7A

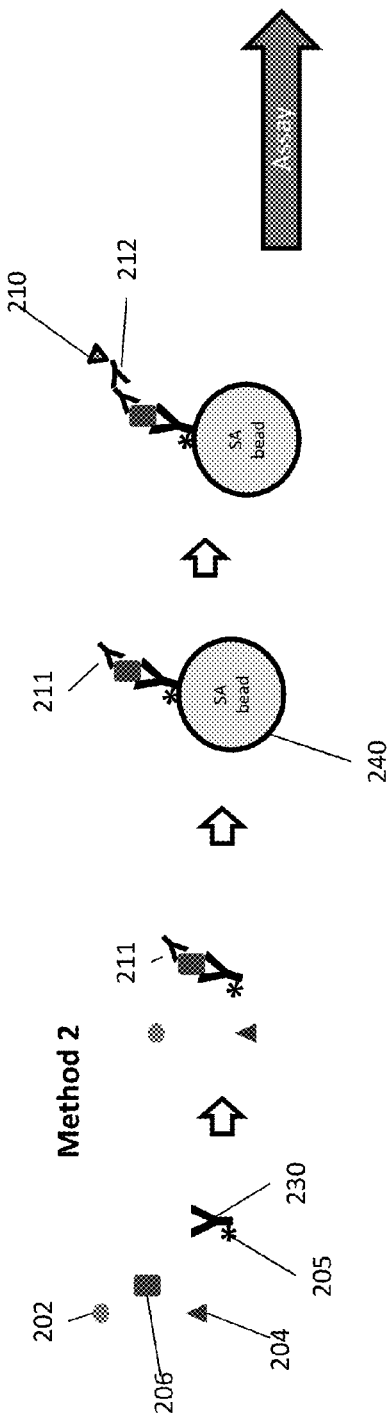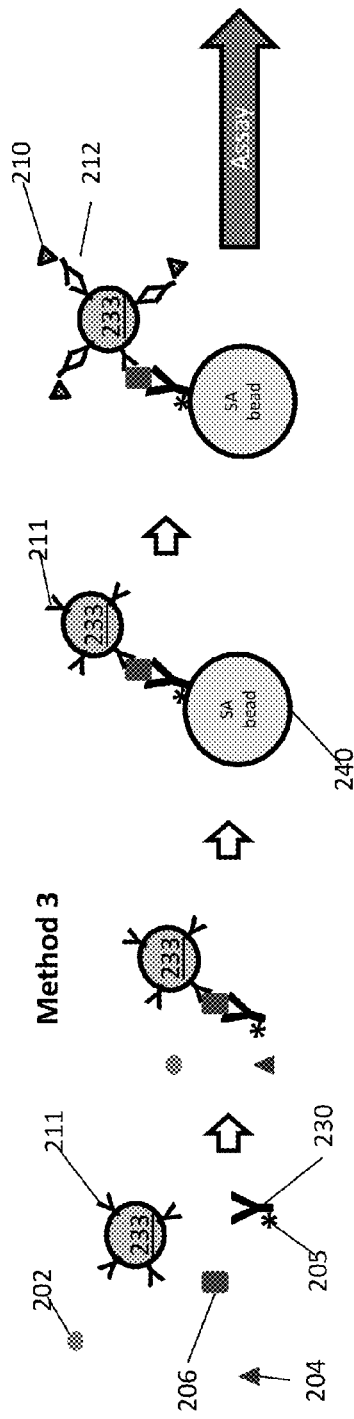
FIG. 8B
FIG. 8C

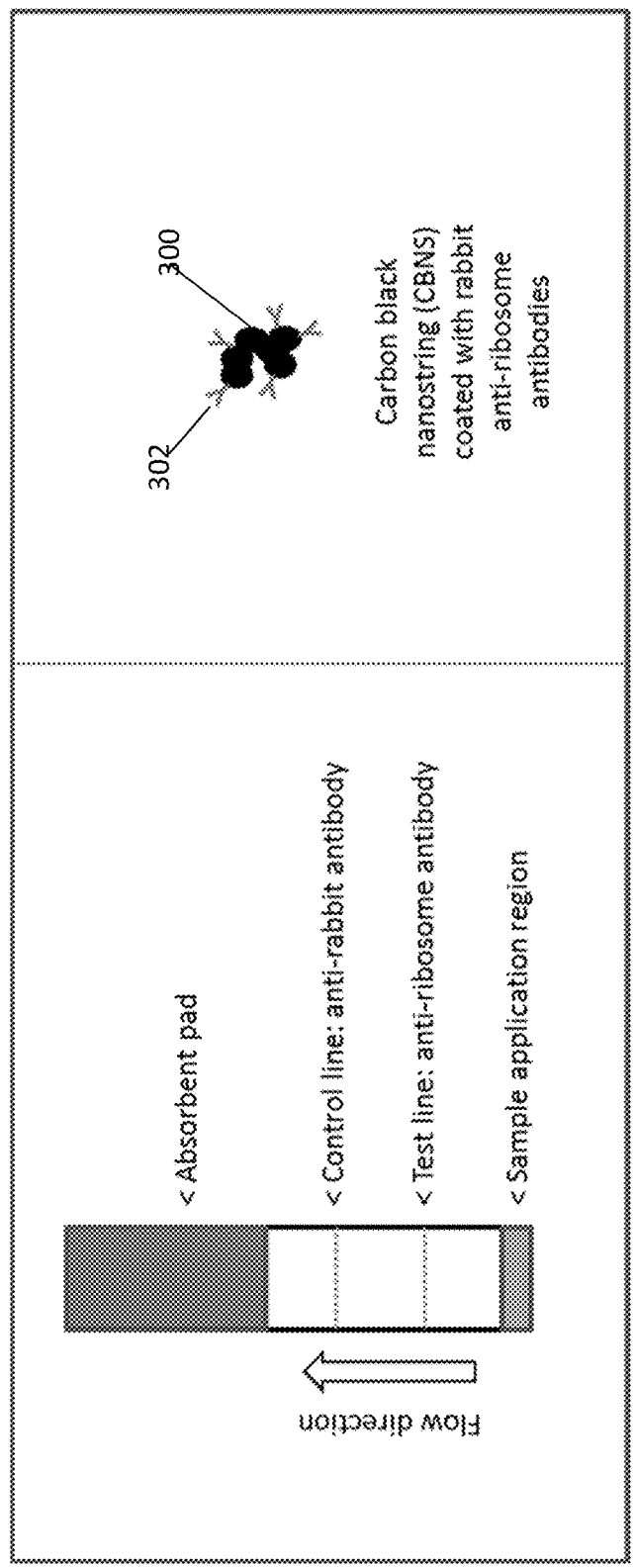

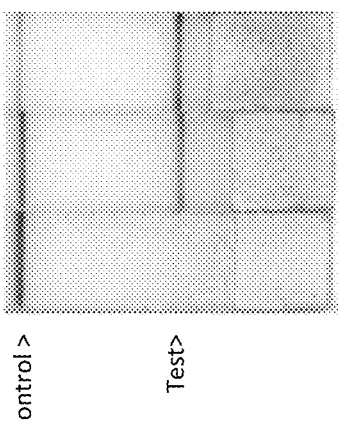

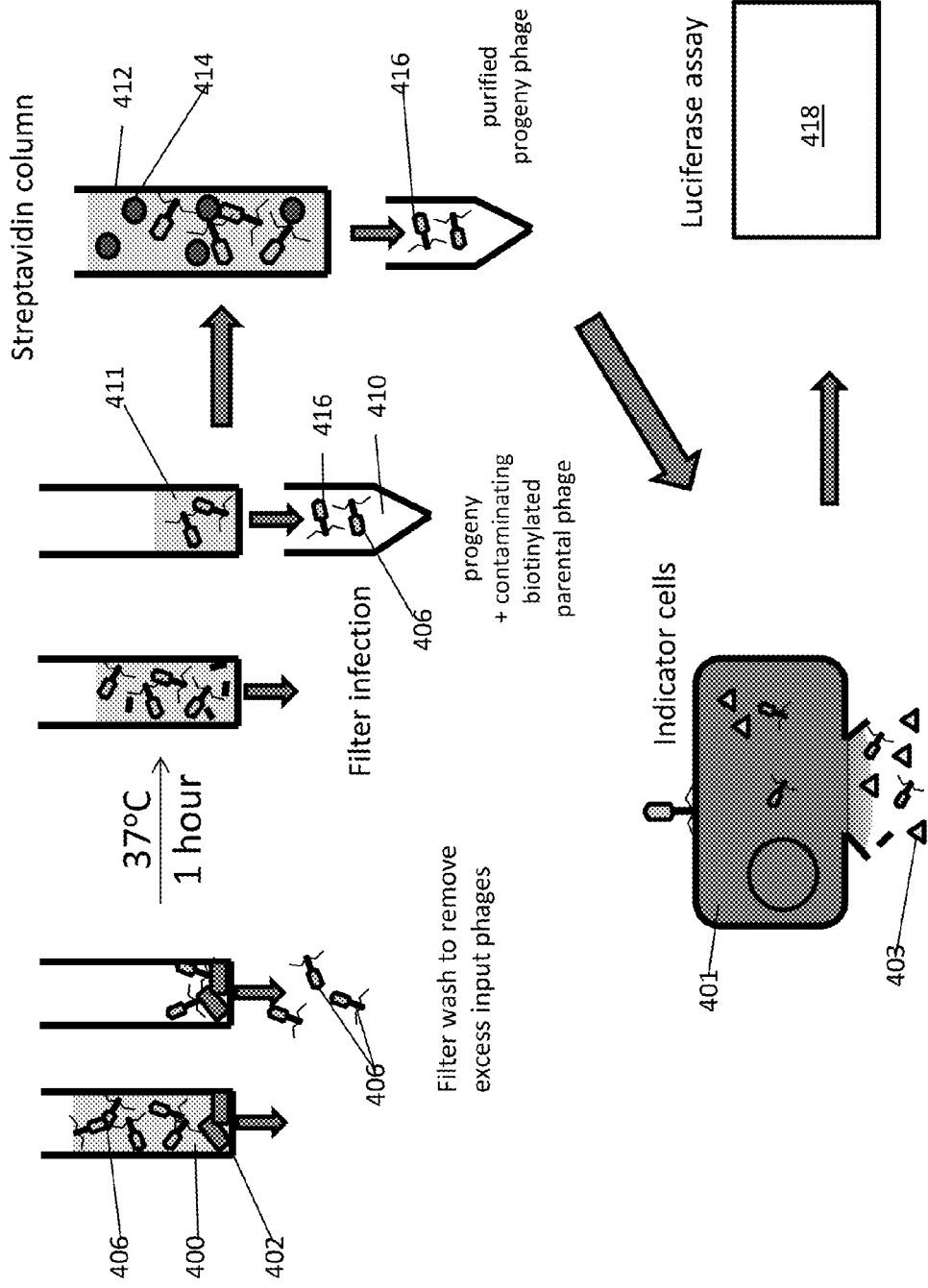

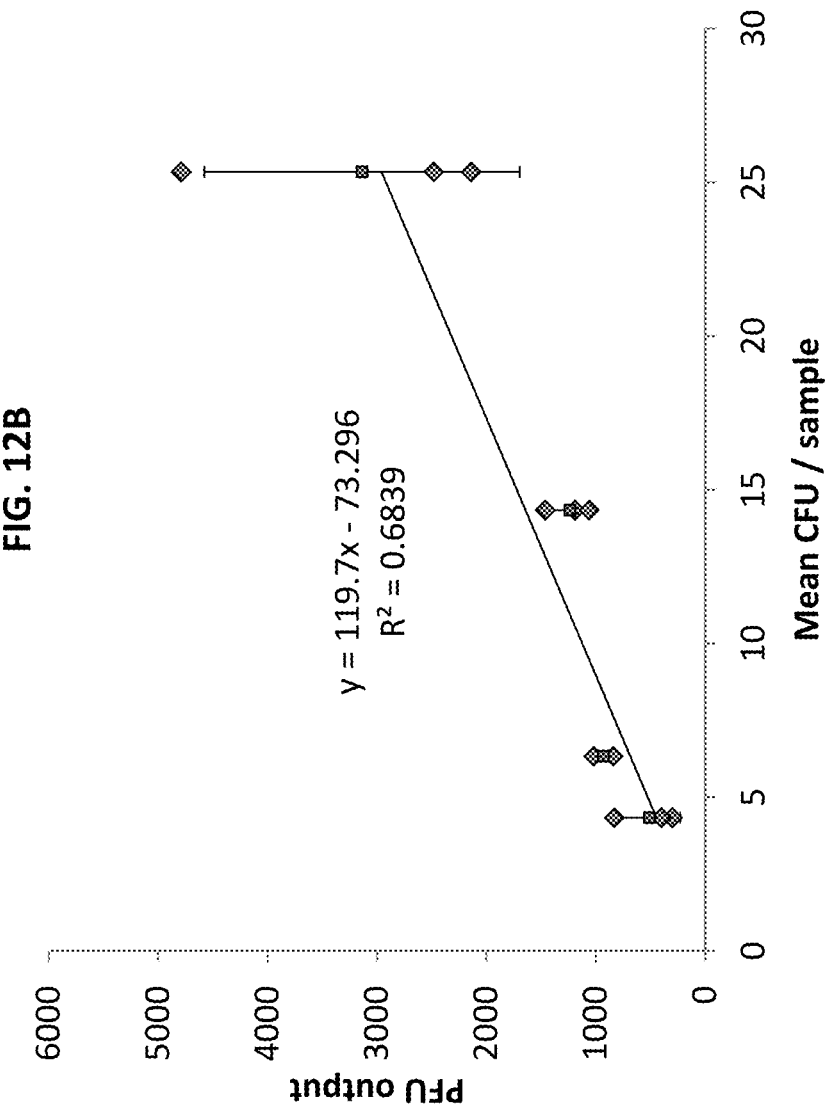

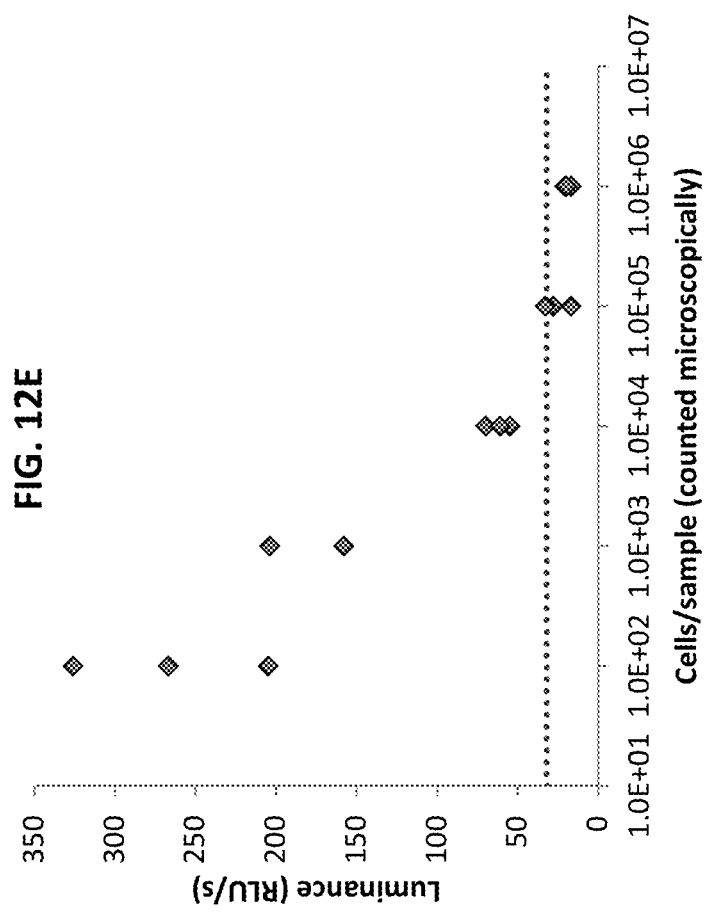

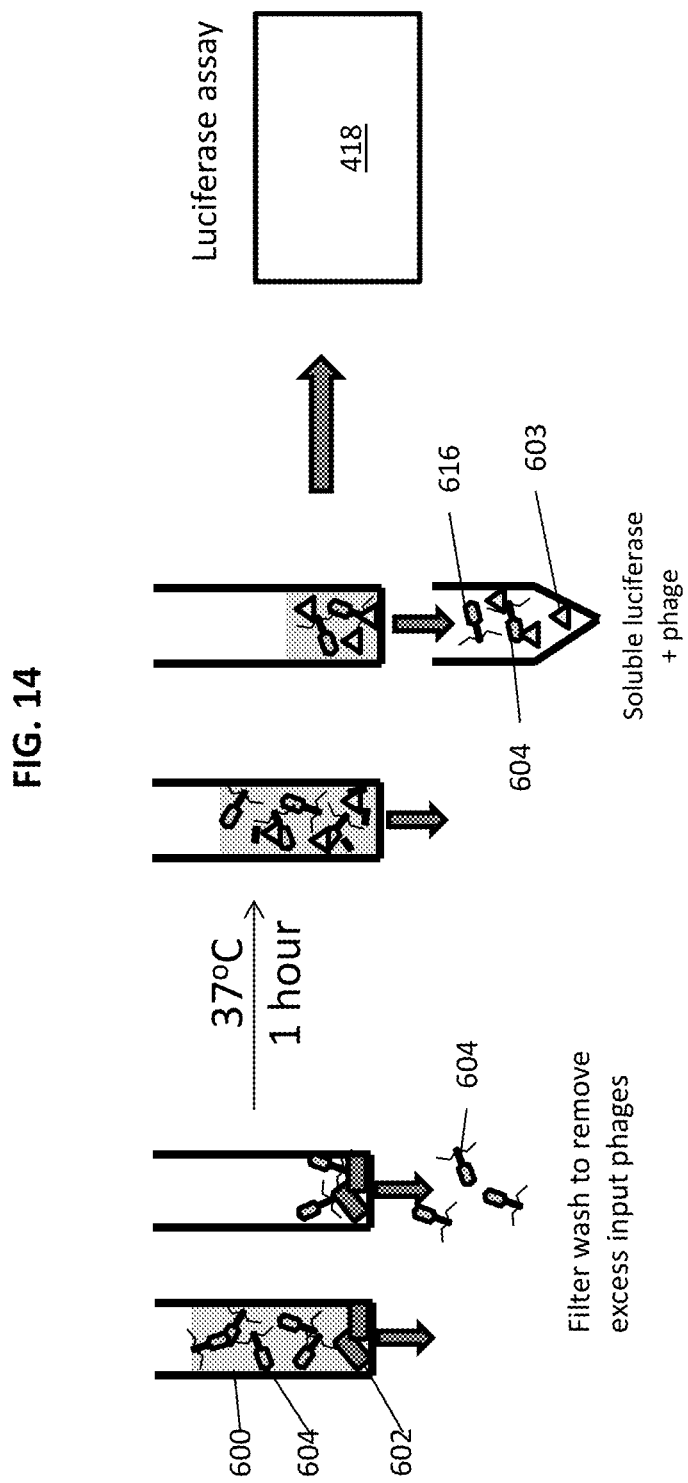

METHODS AND SYSTEMS FOR THE DETECTION OF BACTERIA

This application claims priority to U.S. Provisional Patent Application 61/601,231 filed Feb. 21, 2012. The disclosure of U.S. Provisional Patent Application 61/601,231 is incorporated by reference herein in its entirety.

FIELD OF THE INVENTION

This invention relates to methods and systems for the detection of microorgansims.

BACKGROUND

There is a strong interest in the detection of bacteria and other microorganisms in both biological and food based samples. Bacterial pathogens can cause substantial morbidity among humans and domestic animals, as well as immense economic loss. Also, detection of microorganisms is a high priority within the Food and Drug Administration (FDA) given outbreaks of life-threatening or fatal illness caused by ingestion of food contaminated with certain microorganisms, e.g., *Escherichia coli* or *Salmonella* spp.

Traditional microbiological tests for the detection of bacteria rely on non-selective and selective enrichment cultures followed by plating on selective media and further testing to confirm suspect colonies. Such procedures can require several days. A variety of rapid methods have been investigated and introduced into practice to reduce the time requirement. However, these methods have drawbacks. For example, techniques involving direct immunoassays or gene probes generally require an enrichment step in order to obtain adequate sensitivity. Polymerase chain reaction (PCR) tests also include an amplification step and therefore are capable of both very high sensitivity and selectivity, however, the sample size that can be economically subjected to PCR testing is limited. With dilute bacterial suspensions, most small subsamples will be free of cells and therefore enrichment steps are still required. The time required for biological enrichment is dictated by the growth rate of the target bacterial population of the sample, by the effect of the sample matrix, and by the required sensitivity. For instance, a magnetic-capture PCR system for verotoxigenic *E. coli* can require about 5, 7 and 10 hours of culturing for enrichment to detect 1000, 100, and 1 colony forming unit per milliliter (cfu/ml), respectively, in a model system, and 15 hours of culturing for enrichment to detect 1 cfu per gram (g) in ground beef. In practice, most high sensitivity methods employ an overnight incubation and take about 24 hours overall. Due to the time required for cultivation, these methods can take up to three days, depending upon the organism to be identified and the source of the sample. This lag time is generally unsuitable as the contaminated food, water (or other product) may have made its way into livestock or humans. In addition, increases in antibiotic-resistant bacteria and biodefense considerations make rapid identification of bacterial pathogens in water, food and clinical samples critical priorities worldwide.

Therefore, there is a need for more rapid, simple and sensitive detection and identification of microorganisms, such as bacteria and other potentially pathogenic microorganisms.

SUMMARY OF THE INVENTION

In one aspect, the present invention utilizes the biology of microorganisms for detection of a microorganism in a sample. A variety of microorganisms can be detected using the methods described herein.

For example, in one embodiment, the present invention comprises methods and systems that utilize a plurality of ribosomes that are present in a single microorganism as a means to detect low levels of the microorganism present in a sample. For example, the method may comprise the steps of isolating the microorganism from other components in the sample, lysing the microorganism to release ribosomes present in the microorganism; and detecting the ribosomes, or a constituent of the ribosomes, wherein detection of the ribosomes or a constituent of the ribosomes, indicates that the microorganism is present in the sample. In certain embodiments, the ribosomes and/or ribosomal proteins released from the microorganism may be assayed using a bead-based amplified immunoassay. In yet other embodiments, the present invention may comprise a lateral flow assay in combination with carbon black nanostrings to detect ribosomes and/or ribosomal proteins released from the microorganism.

In other additional and/or alternative aspects, the present invention utilizes the high specificity of agents that can bind to microorganisms or their constituents as a means to detect and isolate low levels of a microorganism (e.g., a single microorganism) present in a sample. For example, in certain embodiments, the method may comprise the steps of isolating at least one bacterium from other components in the sample and infecting the at least one bacterium with a plurality of parental bacteriophage. The method may further comprise lysing the at least one infected bacterium to release progeny bacteriophage present in the bacterium. The method may also comprise detecting the progeny bacteriophage, or a constituent of the progeny bacteriophage, wherein detection of the bacteriophage or a constituent of the bacteriophage, indicates that the bacterium is present in the sample.

The present invention also comprises methods and systems that utilize the specificity of specific binding agents, such as bacteriophage and/or antibodies, to isolate microorganisms from a sample.

Other embodiments described herein utilize progeny bacteriophage and/or bacteria labeled with a detectable moiety to facilitate detection of infected bacteria. For example, the progeny bacteriophage may comprise a detectable biomolecule such as luciferase protein. Or, the progeny bacteriophage may be quantified via infection of bacteria comprising a marker biomolecule such as luciferase protein. Or, the progeny bacteriophage may be quantified using lateral flow assays in conjunction with carbon black nanostrings.

In yet other embodiments, the invention comprises systems (e.g., kits) comprising components for performing the methods disclosed herein.

Thus, embodiments of the present invention rely on bacteriophage-based and ribosome-based methods for amplification of the detection of bacteria. The principles applied herein can be applied to the detection of other microorganisms. Because of the sheer number of the ribosomes present in a microorganism or the rapid increase in the number of infectious agents present in a cell after amplification, it can be easier to detect ribosomes and/or such progeny infectious agents than to detect the microorganisms themselves. In this way, embodiments of the present invention can achieve total amplification of at least 10,000 from a single infected cell.

BRIEF DESCRIPTION OF THE FIGURES

The present invention may be better understood by referring to the following non-limiting figures.

FIG. 5 illustrates an assay comprising isolation of a bacterium from a sample by the use of an immobilized binding agent, cell lysis resulting in release of a plurality of ribosomes, and immunoassay of the ribosomes in accordance with an embodiment of the invention.

FIG. 6 illustrates an assay comprising lysis of a bacterial cell in a sample, isolation of ribosomes released from the cell by the use of an immobilized binding agent, and sandwich immunoassay of the ribosomes in accordance with an embodiment of the invention.

FIG. 7, panels A and B, illustrates a sandwich immunoassay for detection of ribosomes, bacteriophage, or their constituent proteins using a standard immunoassay format (panel A) or a bead amplification of the signal in accordance with an embodiment of the invention (panel B).

FIG. 11 depicts the use of indicator bacteria to detect progeny phage isolated from bacterial cells in accordance with an embodiment of the invention.

FIG. 14 depicts the use of indicator phage with a soluble luciferase to detect progeny phage isolated from bacterial cells in accordance with an embodiment of the invention.

DETAILED DESCRIPTION OF THE INVENTION

Definitions

Figure 1C:
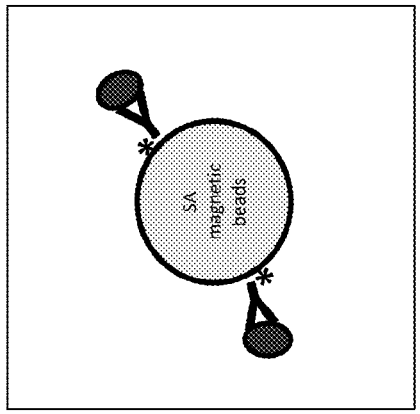
FIG. 1, panels A-E, depicts a schematic of antibody-based capture of intact bacterial cells in solution in accordance with an embodiment of the present invention.
Figure 1B:
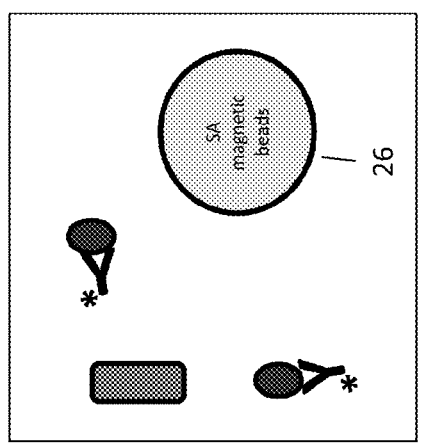
Figure 1A:
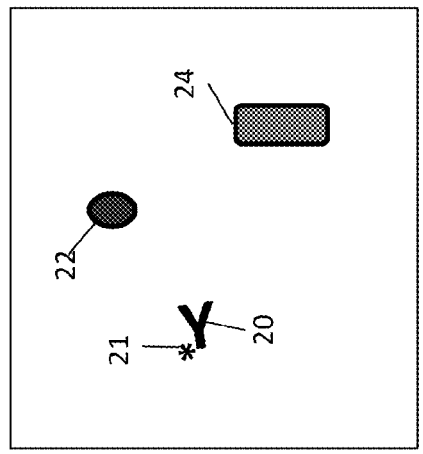
Figure 1D:
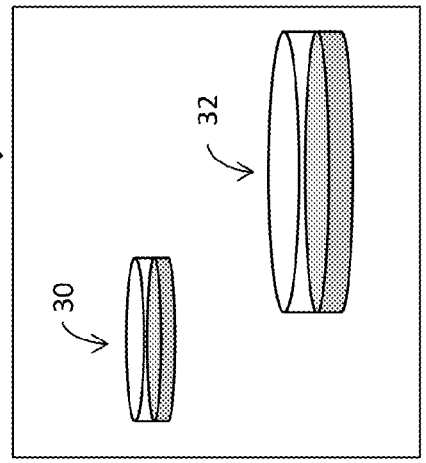
Figure 1E:
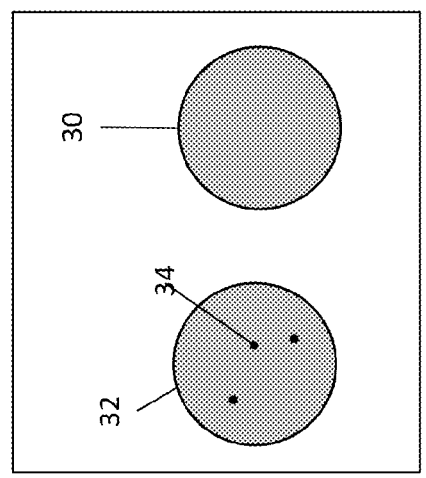

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among samples.

The term "solid support" or "support" means a structure that provides a substrate onto which biomolecules may be bound. For example, a solid support may be an assay well (i.e., such as a microtiter plate), or the solid support may be a location on an array, or a mobile support, such as a bead.

The term "antibody" includes monoclonal antibodies, polyclonal antibodies, synthetic antibodies and chimeric antibodies, e.g., generated by combinatorial mutagenesis and phage display. The term "antibody" also includes mimetics or peptidomimetics of antibodies. Peptidomimetics are compounds based on, or derived from, peptides and proteins. The peptidomimetics of the present invention typically can be obtained by structural modification of a known peptide sequence using unnatural amino acids, conformational restraints, isosteric replacement, and the like.

The term "binding agent" refers to a molecule that can specifically and selectively bind to a second (i.e., different) molecule of interest. The interaction may be non-covalent, for example, as a result of hydrogen-bonding, van der Waals interactions, or electrostatic or hydrophobic interactions, or it may be covalent. The term "soluble binding agent" refers to a binding agent that is not associated with (i.e., covalently or non-covalently bound) to a solid support.

As used herein, an "analyte" refers to a molecule, compound or cell that is being measured. The analyte of interest may, in certain embodiments, interact with a binding agent. As described herein, the term "analyte" may refer to a protein or peptide of interest. An analyte may be an agonist, an antagonist, or a modulator. Or, an analyte may not have a biological effect. Analytes may include small molecules, sugars, oligosaccharides, lipids, peptides, peptidomimetics, organic compounds and the like.

The term "detectable moiety" or "detectable biomolecule" or "reporter" or "indicator moiety" refers to a molecule that can be measured in a quantitative assay. For example, a detectable moiety may comprise an enzyme that may be used to convert a substrate to a product that can be measured (e.g., a visible product). Or, a detectable moiety may be a radioisotope that can be quantified. Or, a detectable moiety may be a fluorophore. Or, a detectable moiety may be a luminescent molecule. Or, other detectable molecules may be used.

As used herein, the term "equivalence zone" indicates the region in a precipitin reaction in which the concentration of antigen and antibody leads to maximal precipitation. Thus, if either antigen or antibody is in excess, precipitation does not occur.

As used herein, "bacteriophage" or "phage" includes one or more of a plurality of bacterial viruses. In this disclosure, the terms "bacteriophage" and "phage" include viruses such as mycobacteriophage (such as for TB and paraTB), mycophage (such as for fungi), mycoplasma phage, and any other term that refers to a virus that can invade living bacteria, fungi, mycoplasma, protozoa, yeasts, and other microscopic living organisms and uses them to replicate itself. Here, "microscopic" means that the largest dimension is one millimeter or less. Bacteriophage are viruses that have evolved in nature to use bacteria as a means of replicating themselves. A phage does this by attaching itself to a bacterium and injecting its DNA (or RNA) into that bacterium, and inducing it to replicate the phage hundreds or even thousands of times. This is referred to as phage amplification.

As used herein, a "bacteriophage marker" is any biological or organic element that can be associated with the presence of bacteriophage. Without limitation, this may be the bacteriophage itself a protein or other molecule incorporated into the phage structure; a protein associated with, or gene product engineered into, the bacteriophage; RNA or DNA associated with the bacteriophage; or any portion of any of the foregoing. As used herein a "bacterial marker" is any biological or organic element that can be used to identify the presence of a bacterium such as constituents released when a bacterium is lysed by a bacteriophage, including cell wall components, bacterial nucleic acids, proteins, enzymes, small molecules, or any portion of the foregoing. For example, in certain embodiments, luciferase protein incorporated by genetic engineering into a structural component of the phage (e.g., fusion with the capsid protein) or as a soluble protein is a bacteriophage marker.

Detection of Microorganisms

The present invention provides methods for detection of microorganisms. Each of the embodiments of the methods and systems of the invention can be applied to detection and quantification of a variety of microorganisms, including bacterial cells, and including pathogens from food, water, clinical and commercial samples. The methods of the present invention provide high detection sensitivity in a short time without the need for traditional biological enrichment. For example, embodiments of the present invention can provide for the detection and quantification of a single microorganism (e.g., bacterial cell) in a sample.

For example, in an embodiment the invention comprises a method for detecting a microorganism of interest comprising the steps of: isolating the microorganism from other components in the sample; lysing the microorganism to release ribosomes present in the microorganism; and detecting the ribosomes, or a constituent of the ribosomes, wherein detection of the ribosomes or a constituent of the ribosomes, indicates that the microorganism is present in the sample.

A variety of microorganisms may be detected using the methods of the invention. In an embodiment, the microorganism comprises at least one of a bacterium, or a fungus, or yeast.

A variety of methods may be used to isolate the microorganism. In an embodiment, the step of isolating the microorganism comprises binding of the microorganism to a binding agent. For example, the step of isolating the microorganism may comprise binding of the microorganism to a binding agent that is bound to a solid support. In an embodiment, the binding agent may be an antibody. Or, where the microorganism is a bacterium, the binding agent may be a bacteriophage and the step of isolating the bacterium utilizes a bacteriophage specific for the bacterium.

A variety of methods may be used to detect ribosomes from the microorganism. In an embodiment, the detection of the ribosomes comprises the use of a primary antibody that recognizes the ribosomes, and at least one secondary antibody that recognizes the primary antibody. Or, the detection of the ribosomes may comprise the use of a primary antibody that recognizes the ribosomes, and at least one second primary antibody that recognizes the ribosomes. In certain embodiments, the second primary antibody is bound to a solid support. In yet other embodiments, the solid support comprises a plurality of second primary antibodies.

In other embodiments, the ribosomes may be detected using a lateral flow assay. For example, in one embodiment, the ribosomes are exposed to (i.e., applied to) a solid support comprising anti-ribosome antibodies and detected by flow of the ribosomes across the surface of the support. In an embodiment, the ribosomes bound to the membrane comprising anti-ribosome antibodies may be visualized using at least one carbon black nano-string comprising additional anti-ribosome antibodies.

Other embodiments of the invention utilize the specificity and multiplicity of infectious agents to detect a microorganism of interest. In another embodiment, the invention comprises a method for detecting a microorganism of interest comprising the steps of: isolating at least one microorganism from other components in the sample; infecting the at least one microorganism with a plurality of a parental infectious agent; lysing the at least one infected microorganism to release progeny infectious agents present in the microorganism; and detecting the progeny infectious agents, or a constituent of the progeny infectious agents, wherein detection of the infectious agent or a constituent of the infectious agent, indicates that the microorganism is present in the sample. In an embodiment the parental infectious agent is separated from the progeny infectious agent. In an embodiment, the microorganism is a bacterium and the infectious agent is a bacteriophage.

For example, in an embodiment, the invention may comprise a method for detecting a microorganism of interest comprising the steps of: isolating at least one bacterium from other components in the sample; infecting the at least one bacterium with a plurality of parental bacteriophage; lysing the at least one infected bacterium to release progeny bacteriophage present in the bacterium; and detecting the progeny bacteriophage, or a constituent of the progeny bacteriophage, wherein detection of the bacteriophage or a constituent of the bacteriophage, indicates that the bacterium is present in the sample. In an embodiment, the parental bacteriophage are separated from the progeny bacteriophage.

The method may comprise a variety of formats for detection of progeny infectious agents, as for example, bacteriophage. For example, in an embodiment, the progeny infectious agent may comprise an indicator moiety. In an embodiment, the indicator moiety in the progeny infectious agent may comprise luciferase fused to a structural protein (e.g., phage capsid protein). In an embodiment, the indicator moiety in the progeny infectious agent may be a detectable moiety that is expressed during replication of the infectious agent, such as, but not limited to, a soluble luciferase protein. In an alternate embodiment, the method may comprise the step of infecting an indicator microorganism with the progeny infectious agent, wherein the indicator microorganism may comprise a protein that is released upon lysis of the indicator microorganism. In an embodiment, the protein release from the indicator microorganism comprises a detectable moiety. For example, in an embodiment, the protein released is a luciferase protein. In an alternate embodiment, progeny infectious agent from infected samples cells and/or indicator cells may be detected by lateral flow assay with carbon black nanostrings.

Or, the protein released from the indicator microorganism may comprise ribosomes. In this way, the method combines the amplification provided by infection with an infectious agent (e.g., bacteriophage) with the amplification provided by ribosome detection.

Isolation of the Microorganism

In certain embodiments, the present invention utilizes the high specificity of agents that can bind to a microorganism of interest as a means to detect low levels of a microorganism (e.g., a single microorganism) present in a sample. For example, in one embodiment, the present invention comprises methods and systems that utilize the specificity of an infectious agent for the isolation of a microorganism from a sample. For example, in certain embodiments, bacteriophage may be used to isolate bacteria.

Or, the invention may use antibodies that are specific for the microorganism. Once isolated, e.g., either by interaction with an antibody, infectious agent, or other binding agent, the microorganism may be lysed for assay of ribosomes and/or progeny infectious agents as described herein.

Thus, in certain embodiments, the step of isolating the microorganism comprises binding of the microorganism to a binding agent that recognizes the microorganism and as such, is used to sequester the microorganism from the remainder of the sample. Methods described herein may serve as means to detect and isolate low levels of a microorganism (e.g., a single microorganism) present in a sample. For example, a single bacterium, which may have a volume of less than one cubic micrometer, can be isolated from a one milliliter sample having a volume of $10^{12}$ cubic micrometers.

In certain embodiments, the present invention comprises methods and systems that utilize the specificity of antibodies for rapid and sensitive isolation of a single bacterial cell from a sample. The method may include the step of contacting the sample with a plurality of antibodies raised against the intact cell. The antibodies may be affinity purified. Additionally and/or alternatively, the antibodies may be biotin-labeled. The method may further comprise allowing the antibodies to bind the bacterium. In the case where the antibody is labeled with biotin, the method may further comprise contacting the sample with a plurality of magnetic streptavidin-coated beads to bind the bacterium-antibody complex, and sequestering the bead-antibody-bacterium complex with a magnet. Or, other methods of purifying the biotin-antibody: bacterium complex may be used. With this method, a bacterium in a one-milliliter sample can be concentrated to about one microliter (~1000-fold), facilitating further detection and/or quantification by methods described herein. For example, once isolated, the bacterium may be lysed for assay of ribosomes as described in more detail herein.

In an alternative embodiment, the present invention comprises methods and systems that utilize the specificity of infectious agents (e.g., viruses specific for a microorganism) for rapid and sensitive isolation of a single microorganism from a sample. Thus, in yet another embodiment, the method may include contacting the sample with a plurality of the specific infectious agent (e.g., bacteriophage in isolation of bacterial cells) bound to a solid support (e.g., a magnetic bead) and allowing the bacteriophage-solid support complexes to find, bind and infect the bacterium. The solid support-bacteriophage-bacterium complex may then be sequestered prior to lysis.

Thus, in certain embodiments, biotinylated phage may be used to infect bacteria in a sample. The biotinylated phage may be immobilized on a streptavidin-coated solid support. In other embodiments, the infectious agent (e.g., bacteriophage) may be immobilized on a solid support using an antibody that specifically binds to the infectious agent (e.g., to the bacteriophage or to a bacteriophage substructure, such as the head).

Subsequently, immobilized input bacteriophage, some of which are bound to bacterial cell envelopes following cell lysis, can be removed from the sample by isolation of the solid support. For example, in one embodiment, the solid support is a magnetic bead, and the phage bound to the bead may be isolated using a magnet.

Or, the biotinylated input phage may be isolated by subsequent purification away from the bacteria and/or progeny phage. For example, the lysate from the infection may be run through a streptavidin column; the parental (input) biotinylated phage will bind to the column, whereas the progeny phage, which are not biotinylated, will be in the flow-through fraction. In this way, the input bacteriophage do not interfere with enumeration of phage progeny produced in the infection.

For example, the method may include the steps of collecting the microorganism (e.g., bacterium), as for example by filtering a sample through a bacteriological filter (e.g., 0.45 um pore size spin filter). Or, other methods of physical isolation of the microorganisms in the sample may be used. The method may further comprise infecting the isolated bacterium with bacteriophage, e.g., at a high multiplicity of infection (MOI), and wherein the bacteriophage comprise a binding moiety (e.g., biotin or other binding agent). The method may also comprise removing at least most of the excess unadsorbed input phage, as for example by washing such unadsorbed phage through the filter used to capture the bacteria.

By using a phage that is linked to a binding agent/solid support to isolate the bacteria, the methods of the present invention can overcome problems associated with distinguishing the phage used to retrieve (isolate) the bacteria (i.e., the input, infecting phage bound to a binding agent or a solid support) from progeny phage (which are not linked to a binding agent or a solid support). A previous approach to this problem has been to destroy the remaining unadsorbed extracellular phage chemically after the target cells are infected. However, the chemical treatment may kill the pathogen cells before they are able to produce new phage particles. In addition, having a large density of the input, infecting phage bound per unit area of a solid support eliminates the potential problem associated with very high multiplicities of infection (MOI) that can lyse bacteria without the production of progeny particles, a process known as "lysis from without".

Bacteriophage may be immobilized on a substrate by one of many procedures known in the art. For example, an antibody specific for the bacteriophage may be used to attach a bacteriophage to a substrate. Alternatively, ligands such as avidin, streptavidin and biotin, may be used. Covalent linkage methods may also be used to attach a bacteriophage to a substrate. Generally, antibodies with specificity for bacteriophage tail proteins should not be used, as the binding of such an antibody to the tail proteins can interfere with the ability of the bacteriophage particle to bind to a host bacterial cell.

An example of a depiction of the isolation of a microorganism is provided in FIG. 1, panels A-E. Thus, as illustrated in FIG. 1, a sample comprising a plurality of bacteria, e.g., bacteria-X and bacteria-Y, 22 and 24, respectively, may be exposed to an antibody specific to bacteria-X, e.g., an anti-bacterium-X antibody 20 as shown in FIG. 1A. In an embodiment, the antibody is complexed to a binding agent, e.g., biotin 21. Upon binding of the bacteria-X 22 to the antibody 20, the complex may be exposed to magnetic beads coated with streptavidin 26 (FIG. 1B). The biotin on the antibody can recognize the streptavidin on the magnetic bead (FIG. 1C). Alternatively, where the primary antibody is not biotinylated, a bead coated with a secondary antibody that recognizes the anti-bacterium-X antibody may be used to coat magnetic beads. Or, a bead coated with Protein A and/or Protein G that recognizes the anti-bacterium antibody may be used. At this point, the bacteria bound to the beads may be isolated. In an embodiment, the efficiency of capture may be quantified by plating the bacteria bound to the beads 32 and the unbound supernatant fraction 30 (FIG. 1D) and counting the resultant colonies 34 (FIG. 1E).

Figure 2:
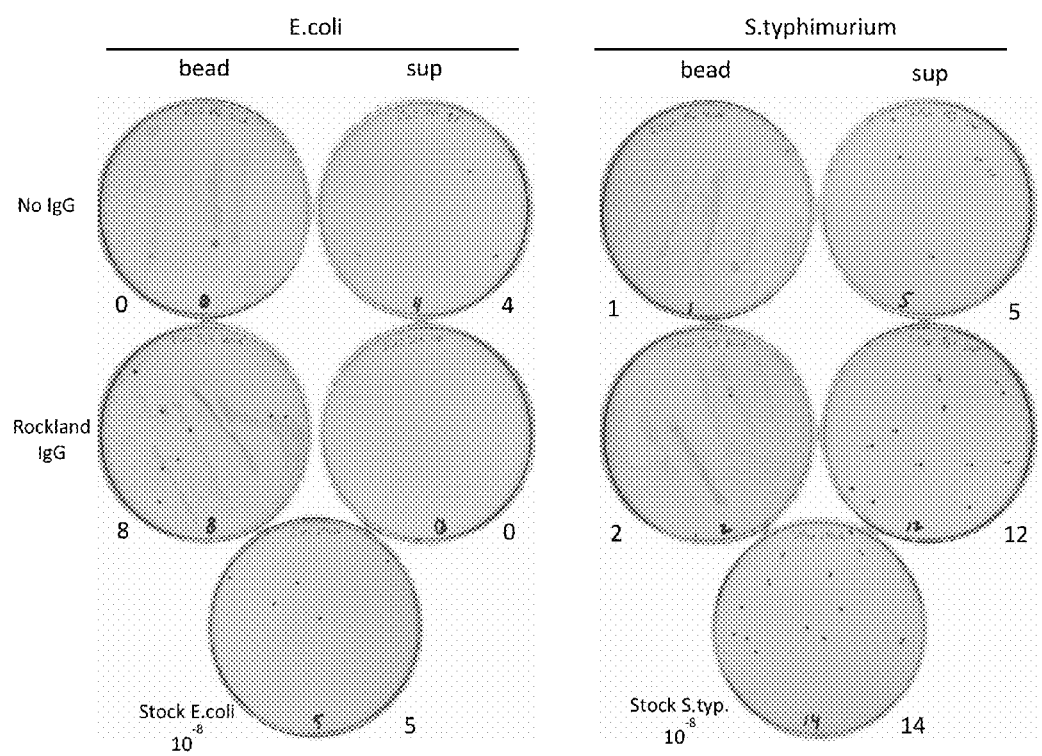
FIG. 2 shows a plate assay of bacteria captured using an antibody-based capture in accordance with an embodiment of the present invention.

FIG. 2 depicts an example experiment of specific capture of *E. coli* but not *S. typhimurim*, from samples by the use of antibodies produced against intact *E. coli*; colony counts are shown below left/right of each plate. In this experiment, magnetic beads coated with streptavidin were used to isolate a complex *E. coli* bound to biotinylated (rabbit) polyclonal antibodies. It was found that the *E. coli* were only present in the bead fraction when specific *E. coli* antibodies were present, and that no bacteria were recovered in the supernatant (unbound) fraction. On the contrary, *S. typhimurium* was found principally in the supernatant fraction when *E. coli*-specific antibodies were used. In the absence of antibody, both types of bacteria were found principally in the supernatant fraction.

Figure 3B:
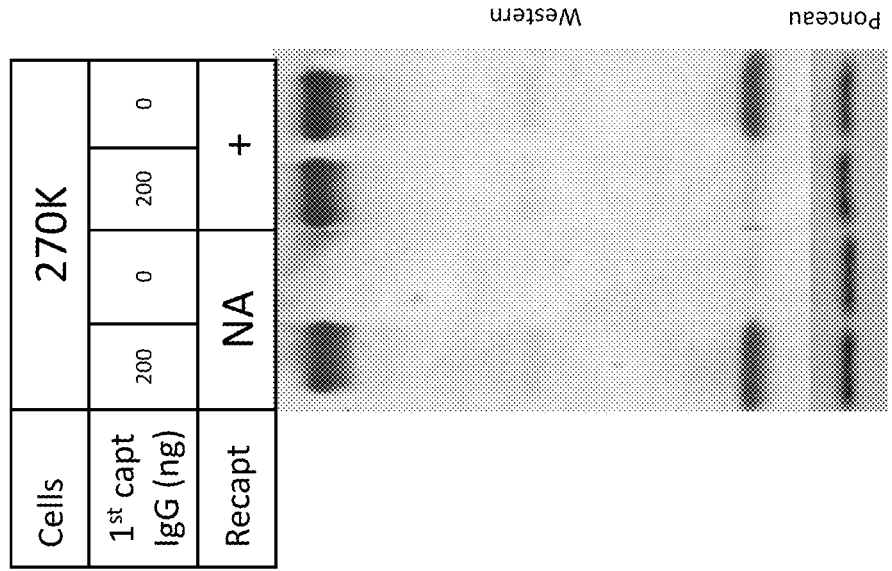
FIG. 3, panels A and B, shows a western blot illustrating ribosomal protein capture using biotinylated anti-ribosomal IgG and magnetic beads linked to streptavidin in accordance with an embodiment of the invention.
Figure 3A:
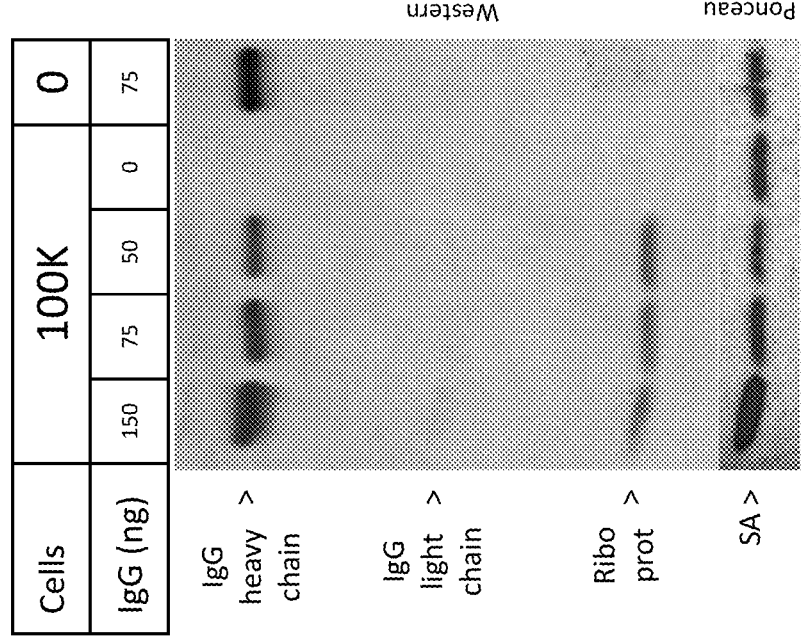

FIGS. 3A and 3B shows Western blot data of ribosomal protein capture from a bacterial (*E. coli*) lysate containing ribosomes dissociated with 6M guanidinium thiocyanate and diluted to 0.6M guanidinium thiocyanate. FIG. 3A shows that anti-ribosome antibodies (IgG) labeled with biotin and streptavidin beads are able to capture ribosomal proteins from solution. It can be seen that when no anti-ribosome antibody is added (IgG=0), the ribosomal proteins ("Ribo prot") are not detected. It can also be seen that 50 ng antibody is capable of binding all the ribosomal proteins from 100,000 cells.

FIG. 3B demonstrates that addition of biotinylated anti-ribosome antibodies and streptavidin beads is sufficient for quantitatively capturing all ribosomes present in solution. In this experiment, lysate from *E. coli* cells in 0.6M guanidine thiocyanate phosphate buffer were incubated with, or without, 200 ng rabbit biotinylated, anti-ribosome IgG. Next, streptavidin (SA) magnetic beads were added to capture the Ab-ribosomal protein complexes. The unbound supernatant was removed from the bead fraction and re-captured ("re-capt") using 200 ng biotinylated antibody and SA magnetic beads. The absence of ribosomal proteins in the recapture experiment with lysate where ribosomal proteins had previously been captured, indicates that the first capture step was sufficient in capturing all of the ribosomal proteins.

Ribosome-Based Signal Amplification

In certain embodiments, the present invention comprises methods and systems that utilize the plurality of ribosomes that are present in a single microorganism as a means to detect low levels of the microorganism present in a sample. In an embodiment, the method is used to assay bacterial cells. However, as disclosed herein, the methods of the invention may be used to measure other types of microbes that contain ribosomes such as, but not limited to fungi, mycoplasmas, protozoa, yeasts, and other microscopic living organisms. Thus, in certain embodiments of the invention, ribosome release, identification and quantification are used to amplify a pathogen cell signal in a natural, commercial or clinical sample.

Ribosomes are compact ribonucleo-protein particles consisting of two subunits that are comprised of proteins containing all amino acids and ribosomal RNAs (rRNAs). Ribosomes from bacteria, archaea and eukaryotes have different structures, proteins and rRNA sequences. Ribosomes may be described in terms of their rate of sedimentation. Bacterial ribosomes generally sediment at about 70S whereas eukaryotic ribosomes generally sediment at about 80S. Bacterial 70S ribosomes have two subunits that sediment at about 50S and 30S, whereas 80S eukaryotic ribosomal subunits sediment at about 60S and 40S.

Figure 4A:
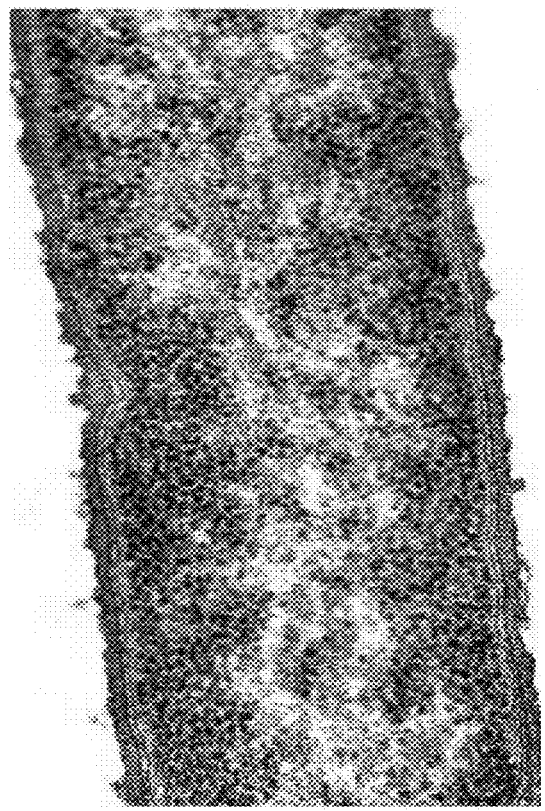
FIG. 4, panels A and B, show electron micrographs of a cell that contains a plurality of ribosomes and purified ribosomes, respectively, where panel A shows an electron micrograph of a portion (about ⅓) of a thin section of *Bacillus subtilis* showing the large number of ribosomes (electron dense dots), and panel B shows a negative stain electron micrograph of purified *E. coli* ribosomes. The cell is approximately 1 μm in diameter and the ribosomes are approximately 20 nm in diameter.

FIG. 4A shows an electron micrograph of a thin section of a *Bacillus subtilis* bacterium, which illustrates the large number of ribosomes (electron-dense dots). The cell shown is about 1 μm in diameter and the ribosomes are about ~0.02 μm (20 nm) in diameter. Only about ⅓ of the cell length is shown. For example, bacterial cells, such as *E. coli*, typically contain about 20,000 ribosomes per cell, which accounts for about one-third to one-fourth of the bacterial protein mass. Thus, the detection of bacterial ribosomes released upon cell lysis can provide a natural amplification of about 20,000 over that of a single cultivable bacterial cell. To produce the same amplification of whole bacterial cells by cultivation and standard enrichment procedures can require 7 hours or more of incubation time, depending on the growth rate of the particular bacterium.

Figure 4B:
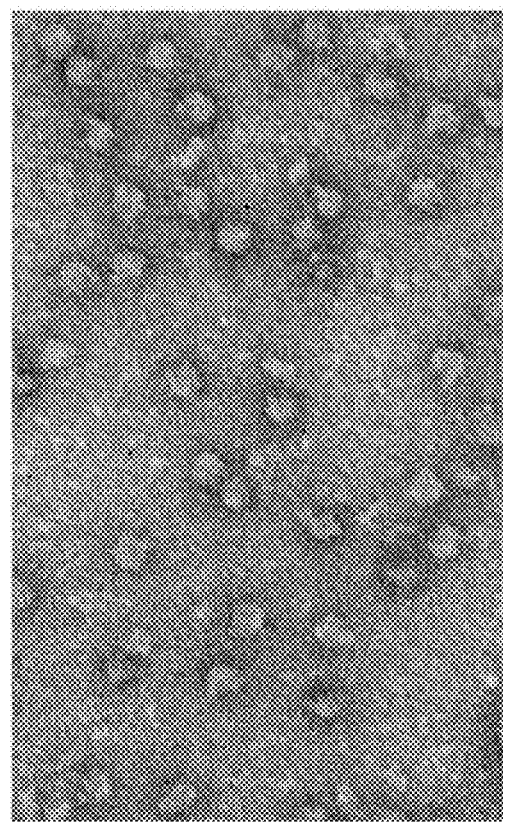

A negative stain electron micrograph of purified ribosomes of E. coli is shown in FIG. 4B. Although the ribosome translation apparatus of bacteria is quite highly conserved, there may be sufficient difference in epitopes of intact ribosomes or isolated ribosomal proteins to distinguish Gram-negative from Gram-positive bacteria, e.g., *E. coli* anti-ribosome antibodies do not recognize and capture *Staphylococcus epidermidis* ribosomal proteins. Slight differences in the epitopes on intact ribosomes of different species may be exploited, e.g., by absorbing sera.

For assay of intact ribosomes, concentrated cells can generally be lysed with an enzyme-detergent mixture to release the ribosomes. In an embodiment, the ribosomes may be isolated by adding ribosome-specific biotinylated antibodies and capturing the ribosome: antibody complex with magnetic streptavidin-coated beads, as described herein. The presence of ribosomes indicates the presence of bacteria specific for the antibodies used in cell concentration, and absence of ribosomes indicates the absence of bacteria specific for the antibodies used in cell concentration.

For example, in one embodiment, the invention comprises a method for detecting a microorganism of interest comprising the steps of isolating the microorganism from other components in the sample; lysing the microorganism to release ribosomes present in the microorganism; and detecting the ribosomes or a constituent of the ribosomes, wherein detection of the ribosomes or a constituent of the ribosomes, indicates that the microorganism is present in the sample. The step of isolating the microorganism may, in certain embodiments, comprise binding of the microorganism to a binding agent that recognizes the microorganism and as such, is used to sequester the microorganism from the remainder of the sample. For example, in certain embodiments, the step of isolating the microorganism may comprise binding of the microorganism to a binding agent (e.g., an antibody or phage) that is bound to a solid support or that comprises a binding agent (e.g., biotin) that recognizes a second agent (e.g., streptavidin or a second antibody) bound to a solid support. For example, either affinity purified polyclonal or monoclonal antibodies that recognize ribosomal proteins from the microbe of interest may be used for detection of ribosomes and ribosomal proteins.

In other additional and/or alternative embodiments, the signal provided by the detection of intact ribosomes may be further amplified by detection of the ribosomal proteins obtained by dissociation of intact ribosomes, e.g., each ribosome of *E. coli* contains 55 distinct proteins, 34 proteins in the 50S subunit and 21 proteins in the 30S subunit. For example, cells isolated from a sample as described herein may be lysed and the ribosomes therein dissociated to individual protein molecules in a single step by the addition of a chaotropic agent (e.g., guanidinium thiocyanate). About one-third of the ribosome mass is protein and about two-thirds of the ribosomal mass is ribosomal RNA (rRNAs). Thus, detection of the 55 ribosomal proteins that constitute each of the 20,000 ribosomes in a single bacterial cell can provide a hypothetical signal amplification of about one million over that of the single cultivable cell. In addition, the 55 distinct protein molecules of each ribosome will have multiple epitopes (amino acid sequences of limited length and variable composition, the number dependent on protein mass) that can bind specific antibodies. In contrast, fewer protein epitopes are displayed on the surface of the intact ribosome; most of the epitopes are buried internally or bound specifically to rRNAs and will not have access to their specific antibodies. Thus, polyclonal or monoclonal antibodies that are specific for ribosomal proteins from the microbe of interest may be used for isolation, detection and quantification of ribosomes or ribosomal proteins from dissociated ribosomes.

Embodiments of the present invention utilize polyclonal rabbit and guinea pig antisera produced against purified ribosomes, for example, of *Escherichia coli, Salmonella typhimurium*, and *Staphylococcus epidermidis*. Or, antibodies to ribosomal proteins from other microorganisms may be used.

For example, and as illustrated in FIG. 5, in one embodiment, a method of the invention may comprise the step of retrieving and concentrating a microorganism 102 (e.g., a bacterium) from a sample 104 by the use of a substrate 106 with a binding agent or bacteriophage 108 specific for the microorganism. In an embodiment, the binding agent 108 is immobilized on a solid support 106 (e.g., polystyrene, silica, or other support as wafers, dipsticks, filters or beads) or is free and subsequently immobilized on a solid support. The immobilized microorganism may then be removed from the sample (e.g., by aspiration, decanting or magnetic force). The microorganism may then be lysed in situ on the solid support and/or released into a small volume (e.g., a microtiter well) 112 for further analysis. For example, in one embodiment, the concentrated microorganism cells are lysed by the addition of a small volume of a mixture of chemicals and enzymes to release ribosomes 114 either directly onto the solid support and/or into a smaller volume 112 such as a microtiter well.

In an additional and/or alternative embodiment, the ribosomal proteins may be detected using anti-ribosome antibodies 116 (e.g., FIG. 5). As is known in the art, the primary anti-ribosome antibodies can be directly labeled (e.g., with a fluorescent biomolecule) 118, or binding of the primary antibodies to the ribosomes can be detected with secondary antibodies.

In yet other embodiments of the methods and systems of the present invention, and as illustrated in FIG. 6, the microorganism cells 102 in a sample 104 may be lysed either in situ (e.g., in the sample) by the addition of a mixture of chemicals and enzymes to release the ribosomes 114. The ribosomes may then be retrieved and concentrated from the sample by the use of a substrate 106 with an immobilized binding agent 122 that specifically binds the ribosomes (e.g., an antibody or other binding agent). The concentrated ribosomes may then be dissociated into subunits 126 with a chaotropic agent, the agent diluted or removed, and the individual proteins 126 identified as for example, using an antibody 117 that is labeled with a detectable moiety 119. For example, the ribosomal protein subunits may be retrieved and concentrated by a method such as, but not limited to, use of a spin concentrator or that removes the dissociating agent, and the protein subunits are identified as described herein.

In alternate embodiments, the ribosomes and/or ribosomal proteins may be identified by a standard immunoassay or by bead-antibody immunoassay amplification methods, such as those described herein, or by other sensitive biochemical, immunochemical, immunofluorescence or biophysical methods as is known in the art. Thus, ELISA, RIA or immunofluorescence assays can be used to detect and quantify the ribosomal proteins.

Or, without removing the dissociating agent, the ribosomal protein subunits can be deposited on a suitable binding substrate in a Reverse-Phase Protein Microarray (RPPMA) method. In an embodiment, the substrate may be blocked to prevent binding of other macromolecules, and the protein subunits identified by linkage to reporter molecules. For example, in a reverse-phase micro-array method, denatured proteins may be arrayed directly onto a nitrocellulose-coated glass slide, probed with primary antibody, and developed with a secondary antibody-reporter complex, such as a biotinylated secondary antibody-QDot complex (see e.g., Geho et al., 2007, Fluorescence-based analysis of cellular protein lysate arrays using quantum dots, 229-237, in "Quantum Dots, Applications in Biology", Methods in Molecular Biology: 374, Bruchez and Hotz, eds., Humana Press).

In another additional and/or alternative embodiment, and as discussed in more detail herein, the intact ribosomes or ribosomal protein molecules may be detected (directly or at a magnification of 50-100×) by clumping of large beads (e.g., 15 μm beads) coated with anti-ribosome antibodies by optimal concentrations of ribosomes or ribosomal proteins at the equivalence zone. The rRNA sequences on the intact ribosome surface may present a field of high negative change that can repel antibodies. In an embodiment, such charges can be neutralized with small basic molecules such as BAC (benzyldimethyalkylammoniumchloride). In this embodiment, the ribosomes, rather than localized to a solid support, can be dispersed in a microtiter well.

Amplified Immunodetection of Bacteriophage Proteins and/or Ribosomal Proteins

In certain aspects, the present invention utilizes the high specificity of biomolecules that have been coupled to a solid support to further amplify a signal as a means to detect low levels of the analytes (e.g., a protein of interest) present in a sample. In certain embodiments, for immunochemical (for example, ELISA or RIA) or immunofluorescence assays in which a protein to be identified is bound directly or through capture antibodies to a passivated surface, signal amplification of about 10,000-fold can be achieved.

Thus, in certain embodiments, the present invention comprises a method for detecting an analyte of interest comprising adding to the analyte of interest a detection support, the detection support comprising a solid support comprising a plurality of molecules of a binding agent that recognizes and binds to the analyte of interest; and detecting at least some of the plurality of binding agent molecules on the detection support. In certain embodiments, the method may further comprise adding a capture support, the capture support comprising at least one capture support binding agent that recognizes and binds to the analyte of interest so as to immobilize the analyte of interest on the capture support. In an embodiment, the analyte of interest is bound to the capture support prior to interacting with the detection support. Or, the analyte of interest may be bound to the capture support after interacting with the detection support. The method may, in certain embodiments, further comprise adding a binding agent that can specifically recognize and bind to at least some of the plurality binding agent molecules on the detection support. In an embodiment, the binding agent that can specifically recognize and bind to at least some of the plurality binding agent molecules on the detection support is a soluble binding agent.

In an embodiment, the capture solid support may be an assay well (i.e., such as a microtiter plate). Or, the capture solid support may be a location on an array, or a mobile support, such as a bead. In an embodiment, the detection support is a mobile support such as bead. In certain embodiments, the analyte of interest may be in solution. Or, the analyte of interest may be a protein inside of a microorganism and/or tissue such that upon fixation, macromolecules in the cell function as a capture support. For example, in an embodiment, the immunoassay amplification methods may be used for in situ detection of proteins.

In one embodiment, the detection support comprising a plurality of molecules of a binding agent that specifically recognize the analyte of interest are added in excess to a sample comprising the analyte of interest. Also in an embodiment, the detection support comprises a plurality of molecules of a detectable moiety. Alternatively, where a binding agent is used to recognize the plurality of binding agent molecules on the detection support, e.g., a secondary antibody, the soluble binding agent may comprise a detectable moiety.

A variety of binding agents may be used in the methods of the invention. For example, the plurality of binding agent molecules attached to the detection support may be either an antibody or an antibody fragment that recognizes the analyte of interest. Additionally and/or alternatively, the binding agent attached to the capture support may be an antibody or an antibody fragment that recognizes the analyte of interest. Additionally and/or alternatively, the binding agent that can specifically recognize and bind to at least some of the plurality binding agent molecules on the detection support (e.g., secondary antibody) may be an antibody or an antibody fragment. Or, the binding agent on any of the capture or detection supports, or the binding agent that can specifically recognize and bind to at least some of the plurality binding agent molecules on the detection support may comprise a protein that binds a non-protein target (i.e., such as a protein that specifically binds to a small molecule analyte of interest, or a receptor that binds to a protein).

In an embodiment, the binding agent that can specifically recognize and bind to at least some of the plurality binding agent molecules on the detection support (e.g., secondary antibody) does not recognize the capture binding agent used to bind the analyte of interest to the capture solid support.

The use of a detection support comprising a plurality of binding agents that recognize the analyte of interest provides amplification of the signal. In alternate embodiments, the detection support comprises more than 1,000, or more than 10,000, or more than 100,000, or more than 500,000, or more than 1,000,000 binding agent molecules specific for the analyte of interest. Thus, in alternate embodiments, the methods of the invention provides an amplification that ranges from 1,000 to 1,000,000,000, or from 1,000 to 100,000,000, or from 5,000 to 10,000,000, or from 10,000 to 1,000,000, or from 10,000 to 500,000, or from 50,000 to 500,000 times the signal seen in a standard, unamplified immunoassay that does not comprise a detection support comprising a plurality of detection binding agents. Or, ranges within these ranges may be achieved.

The use of the detection support and/or the capture support may comprise a variety of formats.

For example, in some embodiments, the analyte of interest may first be bound to the capture support and then allowed to interact with the detection support. Thus, the method may comprise the steps of attaching a plurality of binding agents that can specifically bind to a protein of interest to a capture support. The method may further comprise adding the analyte of interest to the capture support. Next the method may comprise adding a detection support comprising a plurality of detection binding agents specific for the analyte of interest that is bound to the capture support, such that the detection of the plurality of detection binding agents provides amplification of the signal.

Also, in certain embodiments, the method may comprise adding a binding agent that can specifically recognize and bind to the plurality of detection binding agents. In an embodiment, the binding agent that can specifically recognize and bind to the plurality of detection binding agents is a soluble binding agent. The third binding agent may comprise a detectable moiety. Thus, in some embodiments, performing the steps of the method generates a complex comprised of the capture support: capture binding agent: analyte of interest: detection binding agent: detection support: soluble binding agent: detectable moiety.

For example, in several embodiments, the ribosomal proteins and/or proteins from the infectious agent (e.g., bacteriophage proteins) from the microorganism are assayed by use of an assay comprising bead-based amplification provided by a detection support as described herein.

Thus, FIG. 7A illustrates a non-amplified indirect "sandwich" immunoassay system where either ribosomes, ribosomal proteins or progeny phage (or other proteins of interest from the microorganism to be assayed) are immobilized on a solid support and then detected by an antibody. For example, as illustrated in FIG. 7A, the ribosomal or progeny phage protein molecules 206 produced by lysis and dissociation of bacterial cells, including ribosomes, by treatment with a chaotropic agent (e.g., guanidinium thiocyanate), or by dissociation of phage progeny, may be immobilized on a solid surface 214 coated with oriented primary anti-ribosome or anti-phage antibodies 208 (e.g., rabbit). In an embodiment, the solid surface may be coated with protein A/G, and subsequently passivated (i.e., coated to reduce non-specific binding). Alternatively, the antibodies may be covalently bound to the solid surface and the surface passivated. As is shown in FIG. 7A, the immobilized antibodies 208 may specifically recognize the ribosome, ribosomal protein, or phage protein of interest 206, whereas other proteins or biomolecules 202, 204 are not bound. The ribosome, ribosomal protein, or phage protein of interest 206 may then be detected by the addition of a second primary antibody 211 that also recognizes the ribosome, ribosomal protein, or phage protein of interest. For example, the immobilized antibody 208 may be a rabbit anti-ribosome antibody, whereas the second primary antibody 211 may be a guinea pig anti-ribosome antibody. The second primary antibody may then be detected with a secondary antibody (e.g., anti-guinea pig antibody) 212. In an embodiment, the secondary antibody 212 is labeled with a detectable moiety 210. For example, the secondary antibody may be labeled with a fluorescent moiety (e.g., QDOTS®) or an enzyme (e.g., horseradish peroxidase).

FIG. 7B depicts a "sandwich" bead-based amplification immunoassay that may be used to detect ribosomes, ribosomal proteins or progeny phage proteins (or other proteins of interest). In an embodiment, the ribosomes, ribosomal proteins or progeny phage proteins or other proteins of interest are immobilized on a solid support and then detected by an antibody. For example, the protein molecules of interest 206 produced by lysis and dissociation of bacterial cells may be immobilized on a solid surface 214 coated with oriented primary anti-ribosome or anti-phage antibodies 208 (e.g., rabbit). The solid surface may, in certain embodiments, be coated with protein A/G, and subsequently passivated (i.e., coated to reduce non-specific binding). Alternatively, the antibodies may be covalently bound to the solid surface and the surface passivated. Similar to the non-amplified assay, the immobilized antibodies 208 may specifically recognize the ribosome, ribosomal protein, or phage protein of interest 206, whereas other proteins or biomolecules, 202, 204 are not bound.

Next a bead coated with hundreds or thousands or tens of thousands or hundreds of thousands of a second primary antibody 211 that also recognizes the ribosome, ribosomal protein, or phage protein of interest 206 may be added. For example, the immobilized antibody may be a rabbit anti-ribosome antibody, whereas the second primary antibody may be a guinea pig anti-ribosome antibody. In this way, the analyte of interest 206 links the beads comprising the amplifying plurality of second primary antibodies 211 that recognize the analyte of interest 206 to the solid support 214. Finally, a secondary antibody (e.g., anti-guinea pig antibody) 212 that recognizes the second primary antibody 211 is added. In an embodiment, the secondary antibody 212 is labeled with a detectable moiety 210. For example, the third antibody may be labeled with a fluorescent moiety (e.g., QDOTS®) or an enzyme (e.g., horseradish peroxidase). Thus a very large amplification of the signal can originate from a single protein molecule.

Thus, in alternative embodiments for detection of a microorganism in a sample, where dissociation of ribosomes or progeny phage particles to their constituent protein subunits provides additional amplification (as each ribosome of *Escherichia coli* contains 55 proteins, and a bacteriophage particle such as T4 may contain thousands of protein molecules), the high gain amplification immunoassay method may include the steps of isolating the microorganism from other components in a sample and dissociating macromolecular components of the microorganism, including ribosomes therein (or dissociating bacteriophage progeny to protein constituents), in a single step by the use of a chaotropic agent (e.g., 6M guanidinium thiocyanate). The method may further include removal or dilution of the dissociating agent. The method may further include binding biotinylated polyclonal primary ribosome-specific (or bacteriophage-specific) antibodies (e.g., produced in a rabbit) and capture of the protein-antibody complexes by magnetic streptavidin-coated "capture" beads. Next, the method may include binding of "detection" beads coated with a plurality (e.g., tens of thousands) of primary ribosome-specific (or bacteriophage-specific) antibodies produced in another species (e.g., guinea pig). At this point, the method may include the step of binding a plurality of secondary antibodies (e.g., goat anti-guinea pig) conjugated to a detectable moiety (reporter), e.g., horse radish peroxidase, QDOTS®, or Carbon Black NanoStrings; and assay by development of fluorescence or other signal.

In an embodiment, the determinant of the high-gain amplification is the large surface area of the detection beads that can accommodate binding of a large number of the antibodies that are specific to the analyte of interest (e.g., ribosome-specific antibodies). The area occupied by $10^6$ ribosomal protein subunits (the approximate number of ribosomal protein subunits obtained by dissociation of the ribosomes in one bacterial cell) is small, and this area must satisfy accessibility to the beads. In an embodiment, a two-dimensional, confluent array of $10^6$ 1 μm beads will occupy about 1 mm$^2$. For a mobile capture support (e.g., a bead) the number of detection supports of a particular size that can bind can be limited by steric effects. Binding of beads coated with $10^5$ primary antibodies by single protein molecules and subsequent binding of labeled secondary antibodies can be assayed by ELISA, RIA or immunofluorescence, providing high gain amplification.

In yet another embodiment, cells in the sample (or ribosomes released from cells in the sample by the methods described herein) can be concentrated by centrifugation onto the surface of a spin filter of appropriate pore size (typically 0.45 μm for bacteria and 0.02 μm for ribosomes). Concentrated cells may then be lysed in a small volume of buffer (e.g., ~20 μl) as described herein to release the ribosomes. The ribosomes (e.g., about 20,000 from a single bacterial cell) can be transferred from the filter surface to a well of a microtiter plate. At this point, the ribosomes or ribosomal proteins can be identified by formation of a lattice following the addition of ~3,000 large polystyrene beads (typically 15 to 20 μm in diameter) that are coupled to polyclonal antibodies that can recognize multiple epitopes on the ribosomes or ribosomal proteins. Each large bead can bind ~$10^7$ antibodies, and if the beads are precoated with protein G or another protein that complexes to the antibodies, the antibodies are oriented for optimal antigen binding. Lattice formation (bead clumping) as a result of ribosomes or ribosomal proteins bridging anti-ribosome antibodies immobilized on separate beads may be rapid and may be visualized directly without magnification, depending on the size and number of the beads employed, or visualized by light microscopy at a magnification of 50-100×. The use of serial dilutions of ribosomal proteins will identify the equivalence zone where concentrations of bead-bound antibodies and protein molecules are optimal for bead agglutination. Bead-protein G-antibody complexes aggregated (clumped) with a known number of ribosomes or ribosomal proteins may serve as a positive control, and unaggregated bead-protein G-antibody complexes in buffer without ribosomes or ribosomal proteins may serve as a negative control.

FIG. 8 illustrates several alternate embodiments of immunoassays that may be used to detect analytes of interests from a microorganism. In certain embodiments, the assays provide bead-based amplification.

Figure 8A:
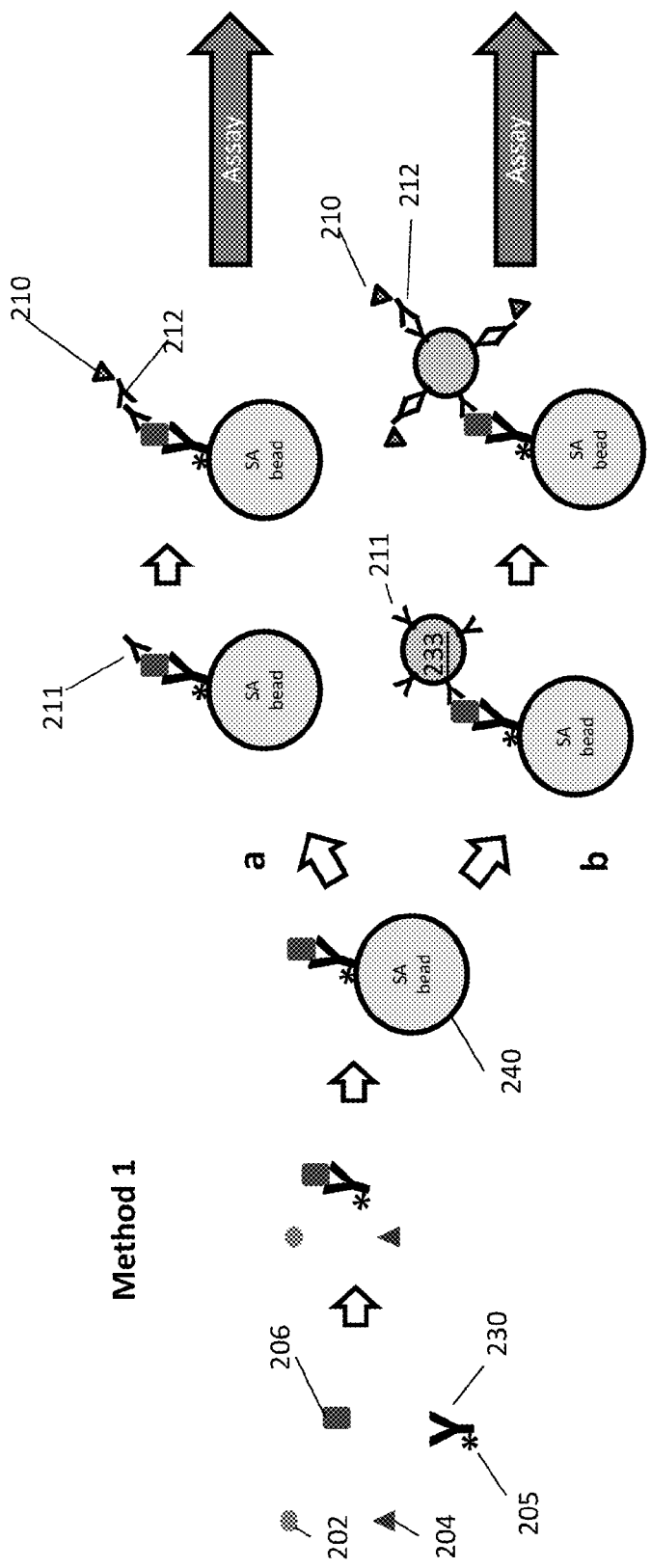
FIG. 8, panels A-F, shows a variety of detection methods for ribosomal proteins in accordance with alternate embodiments of the invention.

As shown in FIG. 8A, Methods 1a and 1b provide example embodiments of an unamplified and amplified immunoassay, respectively, for either ribosomal and/or phage proteins. In these assays, free, primary biotinylated antibody molecules 230 (e.g., rabbit) specific for an analyte of interest 206 (e.g., ribosomal or phage proteins) are added so as to bind to the target molecules in solution. The biotinylated antibody molecules 230 may specifically recognize the analyte of interest 206, whereas other proteins or biomolecules 202, 204 are not bound. At this point, a magnetic streptavidin-coated "capture" bead or beads 240 (e.g., about one micrometer in diameter) may be added to bind the biotinylated antibody-protein complexes quantitatively. In an embodiment, the method may include blocking the bead-protein complexes by the addition of biotin and bovine serum albumin (BSA).

At this point, in the amplified assay (Method 1b), a "detection" bead or beads 233 coated with hundreds, to thousands, to tens of thousands, to hundreds of thousands or more molecules of a second primary anti-ribosome antibody 211 produced in a different species (e.g., guinea pig) is added to bind to open, unoccupied epitopes on the ribosomal protein molecules. The amount of second primary antibody molecules 211 may be detected using a secondary antibody molecules (e.g., anti-guinea pig antibody) 212 that recognize the second primary antibody 211. In an embodiment, the secondary antibody molecules 212 are labeled with a detectable moiety 210. For example, the secondary antibody may be labeled with a fluorescent moiety (e.g., QDOTS®) or an enzyme (e.g., horseradish peroxidase). Thus a very large amplification of the signal originates from a single protein molecule due to the presence of a large number of second primary antibody molecules on the detection bead. In contrast and for comparison, an indirect immunofluorescence sandwich assay utilizing capture beads but no amplifying detection bead is illustrated in Method 1a.

FIG. 8B (Method 2) illustrates an alternate form of the unamplified assay of Method 1a, but where the second primary antibody molecules 211 and the first primary antibody molecules 230 are added simultaneously, and prior to the addition of the streptavidin bead or beads 240.

FIG. 8C (Method 3) illustrates an alternate form of the amplified assay of Method 1b, but where the first primary antibody molecules 230 and detection bead or beads 233 coated with second primary anti-ribosome antibody molecules 211 produced in a different species (e.g., guinea pig) are added prior to the addition of the streptavidin capture bead or beads 240 that recognize the first primary antibody molecules 230. In an embodiment, this may promote formation of a complex between the analyte of interest 206 and the detection support bead or beads 233 and the first primary antibody molecules 230.

Figure 8D:
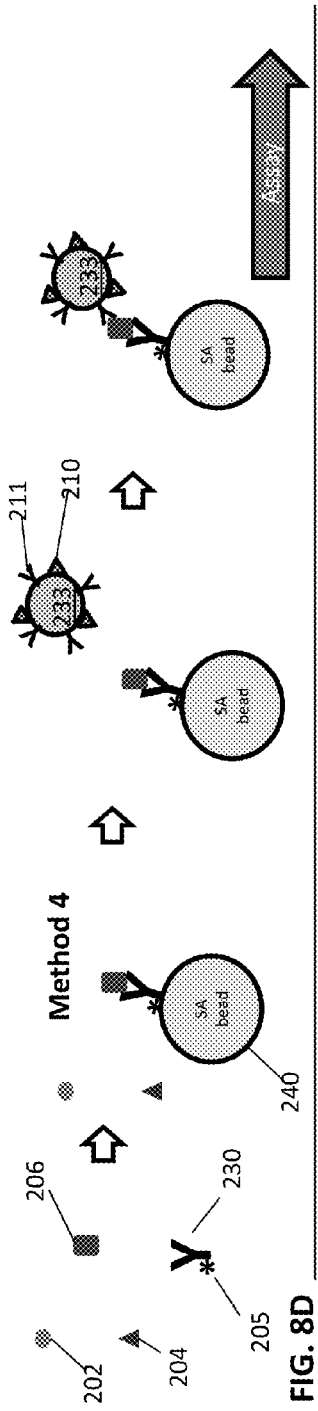

FIG. 8D (Method 4) illustrates an alternate form of the amplified assay of Method 1b, but where the detection bead or beads 233 coated with a plurality of second primary anti-ribosome antibody molecules 211 produced in a different species (e.g., guinea pig) comprise a plurality of molecules of a detectable moiety 210 as part of detection bead or beads 233 (e.g., by covalent attachment or coated on the surface) rather than being bound to the second primary anti-ribosome antibody molecules 211. The detectable moiety 210 may comprise a fluorescent moiety (e.g., QDOTS®) or an enzyme (e.g., horseradish peroxidase). In an embodiment, this method may allow for the use of fewer detection binding agents (e.g., second primary anti-ribosome antibodies 211) if the detection support comprises a plurality of detectable moieties. For example, the ratio of detectable moieties 210: detection binding agents 211 on the detection support 233 may be 1:1, or 5:1, or 10:1, or 100:1, or 500:1, or 1000:1, 10,000:1 or greater. The detectable moiety may comprise a fluorescent moiety (e.g., QDOTS®) or an enzyme (e.g., horseradish peroxidase).

Figure 8E:
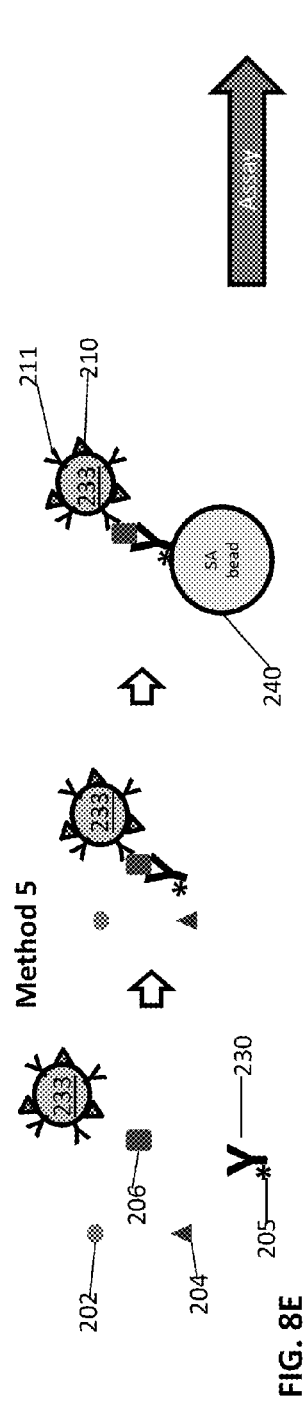

FIG. 8E (Method 5) illustrates an alternate form of the assay of Method 4, but where the detection bead or beads 233 coated with second primary anti-ribosome antibody molecules 211 produced in a different species (e.g., guinea pig) and a detectable moiety 210 are added prior to the addition of the streptavidin bead or beads 240 that recognize the first primary antibody molecules 230. In an embodiment, this may promote formation of a complex between the analyte of interest 206 and the detection support bead or beads 233 and the first primary antibody molecules 230.

Figure 8F:
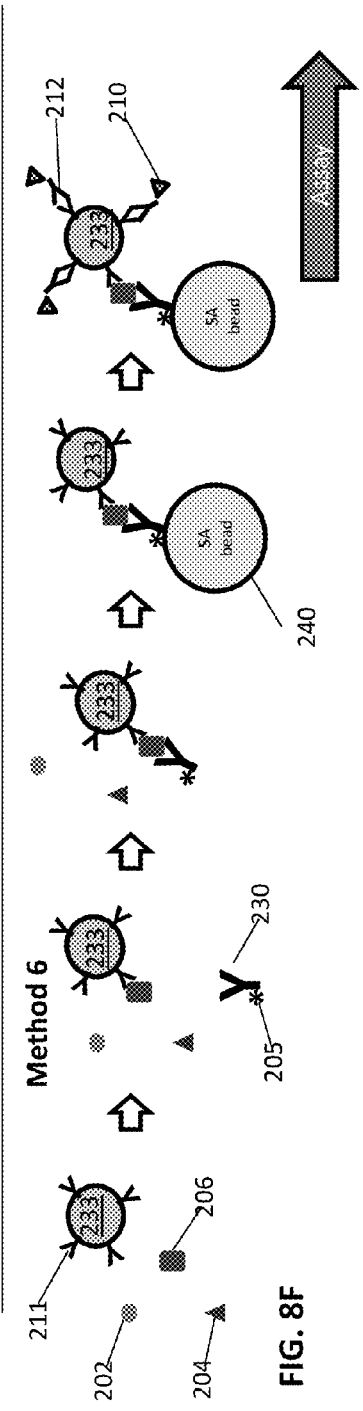

FIG. 8F (Method 6) illustrates an alternate form of Method 3, but where the where the detection bead or beads 233 coated with second primary anti-ribosome antibody molecules 211 produced in a different species (e.g., guinea pig) are added prior to the addition of the first primary antibody molecules 230 and the streptavidin bead or beads 240 that recognize the first primary antibody molecules 230. In an embodiment, this may promote formation of a complex between the analyte of interest 206 and the detection support bead or beads 233.

Figure 9:
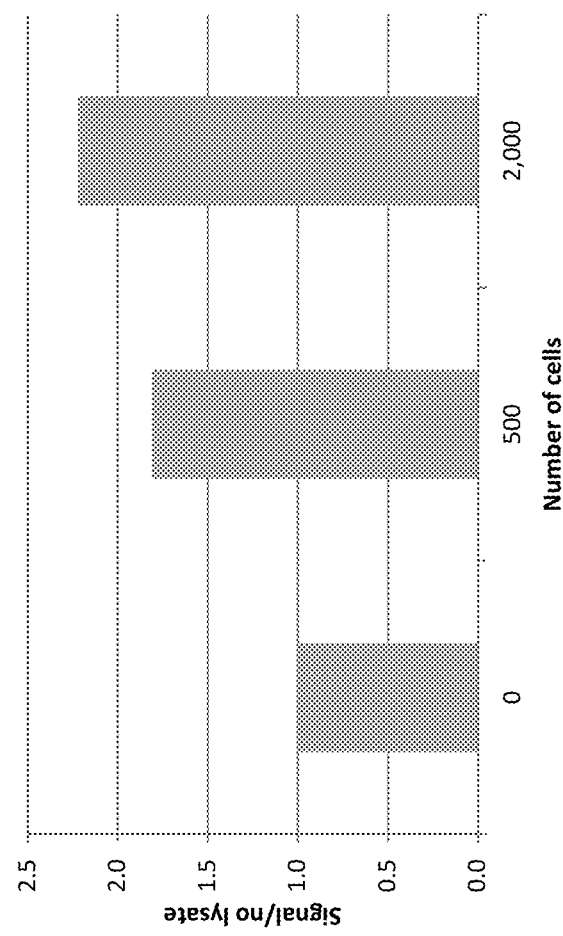
FIG. 9 shows results for detection of ribosomal proteins in accordance with an embodiment of the invention where the x axis indicates the number of bacterial cells and the y axis indicates the signal relative to a control that had no bacterial cells.

FIG. 9 shows results with the Method 6 showing detection of ribosomes from the equivalent of 500 or 2,000 E. coli cells. The x axis indicates the number of bacterial cells and the y axis indicates the signal relative to a control that had no bacterial cells.

It can be important that the secondary antibody and/or the detection second primary antibody do not bind to the capture support antibody, as such binding could lead to background. Thus, in certain embodiments, the step of detection comprises addition of a secondary antibody that recognizes the detection primary antibody agent on the detection bead, but wherein the secondary antibody does not recognize the capture binding agent (e.g., first primary antibody) used to bind the protein of interest to the capture support.

In certain embodiments, the capture and/or detection solid supports may be treated with a passivating agent. For example, in certain embodiments the analyte of interest may be captured on a passivated surface (i.e., a surface that has been treated to reduce non-specific binding). One such passivating agent is BSA. Additionally and/or alternatively, where the binding agent used is an antibody, the capture and/or detection solid supports may be coated with protein A, protein G, protein A/G, protein L, or another agent that binds with high affinity to the binding agent antibody. These proteins bind the Fc domain of antibodies and thus can orient the binding of antibodies that recognize the protein or proteins of interest.

The detection and/or capture supports may be polystyrene beads or beads made of a similar or other material, such that the beads that can be coated with proteins, but do not react with other components in the assay. In certain embodiments the beads are sufficiently large such that a plurality of the antibody molecules may be attached to the bead. For example, the beads may range in size from about 0.1 to 50, or 0.2 to 40, or 0.3 to 30, or 1 to 20, or 1 to 15 or about 1 to 3 μm in diameter. The size of the beads may depend upon the size of the assay to be performed. For an assay performed in a microtiter well, beads of about 1 micrometer (μm) may be used.

In alternate embodiments, the detection support may comprise a plurality of detection binding agents. For example, in alternate embodiments, the number of binding agents on the detection support may be greater than 100, or greater than 500, or greater than 1,000, or greater than 5,000, or greater than 10,000, or greater than 20,000, or greater than 50,000, or greater than 100,000, or greater than 500,000, or greater than 1,000,000 molecules of the detection binding agent. For example, in an embodiment, the detection support may comprise a bead that is coated with tens or hundreds of thousands of antibody molecules. In alternate embodiments, there may be about 10,000 to 10,000,000 or about 50,000 to 1,000,000, or about 100,000 to 500,000 binding agent molecules (e.g., a primary antibody) for a detection support bead that is about 15 μm in diameter. For detection support beads of different sizes, corresponding surface coverage can be used. Thus, in alternate embodiments, the methods of the invention provides an amplification that ranges from 1,000 to 1,000,000,000, or from 1,000 to 100,000,000, or from 5,000 to 10,000,000, or from 10,000 to 1,000,000, or from 10,000 to 500,000, or from 50,000 to 500,000 times the signal seen in a standard, unamplified immunoassay that does not comprise a detection support comprising a plurality of detection binding agents. Or, ranges within these ranges may be achieved In certain embodiments the detection support beads are sufficiently large such that a plurality of the binding agent molecules may be attached to the bead. For example, the beads may range in size from about 0.1 to 50, or 0.2 to 40, or 0.5 to 30, or 1 to 20, or 1 to 15 or about 1 to 3 μm in diameter. Where the binding agent to be attached to the bead is an antibody, beads commercially available pre-coated with protein G, protein A, or proteins A/G may be used as these proteins bind the Fc domain of antibodies, orienting the antibodies such that the Fab domains are free to bind epitopes of antigens.

As described above, a binding agent (e.g., a secondary antibody that recognizes the second primary antibody on the detection support) complexed with an enzyme or fluorescent material (QDOTS® or other fluorescent label) may be added to bind to the large number of antibodies used as detection binding agents on a detection support. Immunochemical (for example, ELISA) assay or excitation and visualization of fluorescent material in an appropriate emission imaging system may be used to quantify the protein. In an embodiment, the key to the large signal amplification factor provided by this method is the large surface area of the detection support that can accommodate binding of detection binding agents. For example, for antibodies, about >10,000 and >100,000 molecules may be used to coat 1 μm and 2.8 μm beads, respectively.

Detection of Ribosomes by a Lateral Flow Assay (LFA)

In one embodiment, ribosomes may be detected using a lateral flow assay (LFA) or immunochromatographic assay. Such assays can be quick and easy to perform and may produce a visual result within an hour. In an embodiment, the assay may comprise an ultrasensitive lateral flow assay using carbon black nano-strings (CBNS), which serves as the antibody-support and result readout (Lonnberg et al., J. Immunol. Methods, 339: 236-244 (2008)).

For example, in certain embodiments, the lateral flow assay may comprise a solid support that allows for flow of molecules in a single direction. In an embodiment, the solid support may comprise a strip having a longer length than width (FIG. 10A). The strip may consist of a membrane (e.g., a nitrocellulose membrane or other type of absorbent substrate) and an absorbent pad in contact with the membrane (FIG. 10A). In an embodiment, the membrane may contain a test line with anti-ribosome antibodies from a first species (e.g., rabbit) that recognize the analyte of interest (e.g., ribosomes, ribosomal proteins, phage proteins), and a control line with secondary antibodies that recognize antibodies from the first species (e.g., goat anti-rabbit antibodies). Also shown in FIG. 10A are the carbon black nanostrings 300 coated with an anti-ribosome antibody 302.

Figure 10B:
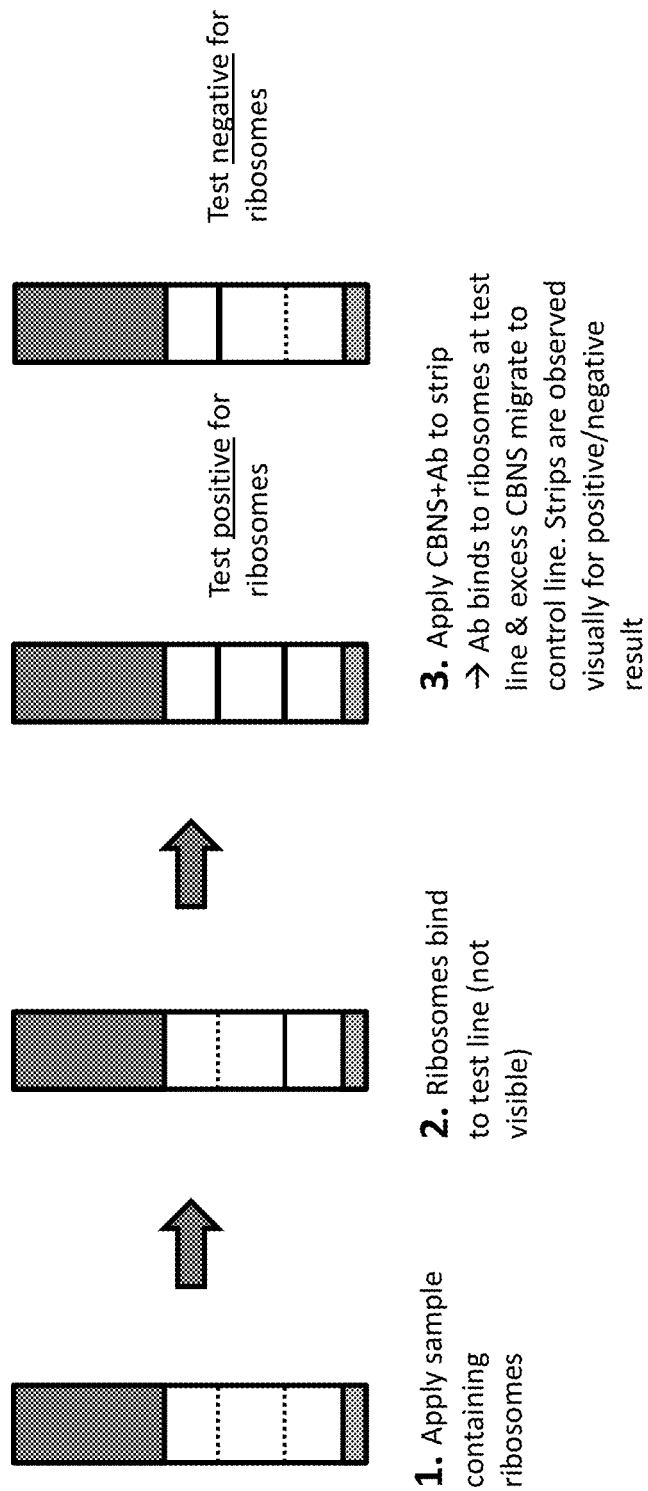
FIG. 10, panels A-D, depicts the use of a lateral flow assay for detection of ribosomes in accordance with alternate embodiments of the invention, where panel A shows a schematic of a lateral flow strip and a depiction of a carbon black nanostring (CBNS); panel B shows a schematic representation of the use of a lateral flow assay to measure ribosomes; and panels C and D show measurement of ribosomes using a lateral flow assay and alternate development methods.

In an embodiment, the assay may be performed by applying the sample to the bottom of the membrane ("sample application region") (FIG. 10B) and allowing the sample to flow by capillary action across the surface of the membrane as shown in FIG. 10A. The analyte of interest present in the sample can thus interact with, and bind to, the immobilized antibodies at the test line (e.g., anti-ribosome antibodies for ribosome analytes), while the rest of the material in the sample will continue into the absorbent pad. The strips may then be incubated with carbon black nanostrings pre-coated with antibodies (CBNS-Ab) that also recognize the analyte of interest (e.g., rabbit anti-ribosome antibodies). In an embodiment, the LFA strips have antibody from total serum IgG whereas the IgG on CBNS-Ab is affinity purified with the antigen of interest. The CBNS-Ab complexes are allowed to flow across the nitrocellulose surface. In this way, the CBNS-Ab complexes can interact with ribosomes bound to the test line. This interaction may be visualized as a gray to black line (FIG. 10B). Any unbound CBNS-Ab can continue up the strip and bind to the anti-rabbit control line, which also results in a gray/black line (FIG. 10B). If the sample does not contain ribosomal proteins, no line will form at the position of the test line but a line will form at the position of the control line.

FIGS. 10C and 10D show detection of ribosomes from *E. coli* using such a lateral flow assay with carbon black nanostring coated with rabbit anti-ribosome antibodies. Thus, FIG. 10 C shows detection of 10 ng of ribosomes using CBNS coated with rabbit anti-ribosome antibodies and the presence of ribosomes in the sample seen as a line at the test line position. The line at the control indicates that the CBNS-Ab migrated up the strip.

In certain embodiments, the sensitivity in the CBNS-LFA system may be increased by decreasing the area of the test line in order to concentrate the CBNS into a smaller area so as to increase the intensity of the line. In another embodiment, a CBNS secondary antibody complex that will bind to the CBNS-Ab already localized on the test line may be used to further increase the intensity of the signal. A third method may incorporate an enzyme, e.g., horseradish peroxidase (HRP) onto the primary antibody-CBNS complex or a secondary antibody-CBNS complex so that an HRP substrate can be added directly to the strip to increase the line intensity by converting the substrate into a colored product. Additionally and/or alternatively, biotinylated antibodies on the CBNS may be used in conjunction with soluble streptavidin-HRP (SA-HRP) or SA-HRP bound to CBNS as a means to increase the signal. FIG. 10D shows an experiment using CBNS-biotinylated anti-ribosome antibodies and developed by visualization of the CBNS-biotinylated anti-ribosome antibodies (top panel) as well as by the addition of CBNS complexed to streptavidin conjugated to horse radish peroxidase (SA-HRP-CBNS), and then a colorimetric horse radish peroxidase substrate added (lower panel). It can be seen that detection of as little as 5 ng ribosomes is possible using this method.

Amplification Provided by Infectious Agents

In another embodiment, the present invention provides a rapid and sensitive method of detecting a microorganism in a sample, the method including: contacting the sample with an infectious agent that is either free or bound to a binding agent that is bound to a solid support, wherein the infectious agent is specific to the microbe and so can isolate the microbe from the sample. For example, in certain embodiments, the microbe of interest is a bacterium, and the infectious agent is one or more bacteriophage. Or, for other types of microorganisms, other infectious agents may be used.

As described above, bacteriophage are viruses that attach to particular bacteria and inject their genetic material. The bacteriophage then use the machinery of the bacteria to replicate themselves a hundred or hundreds of times in a short time period. Some bacteriophage are lytic, meaning that they rupture the host bacteria, and the replicated phage (progeny) are released into the environment in order to seek out and infect other bacteria.

Additionally, most bacteriophage are specific to particular bacteria in that replication of a particular bacteriophage only occurs in specific bacteria. Therefore, the presence of amplified bacteriophage identifies the presence of the bacteria to which it is specific. Further, since bacteriophage can infect a bacterium and produce progeny phage in as little as an hour or less, the detection time is significantly reduced compared to detection of a cultivatable cell.

Whether the bacteriophage has infected the bacteria can be determined by an assay that can identify the presence of bacteriophage progeny, or bacteriophage marker, or a bacterial marker that is detected upon infection with parental phage or progeny phage. In an embodiment, the assay not only can identify the bacteriophage, bacteriophage marker and/or bacterial marker, but also the quantity or concentration of the bacteriophage, bacteriophage marker, or bacterial marker.

For example, in one embodiment, the present invention provides an ultrasensitive bacteriophage-based assay for the rapid detection and quantification of bacterial pathogens. In one embodiment, the invention may comprise a method for detecting a bacterium comprising the steps of: isolating at least one bacterium from other components in the sample and infecting the at least one bacterium with bacteriophage. The method may also comprise the step of removing most of the unadsorbed input phage. The method may also include the step of incubating the infected cell to promote phage replication and cell lysis to release progeny phage and detecting the progeny bacteriophage, or a constituent of dissociated progeny bacteriophage, wherein detection of the bacteriophage or a constituent of the bacteriophage (i.e., a bacteriophage marker), indicates that the bacterium is present in the sample. The method may further comprise removing remaining input phage prior to detecting the progeny phage.

Other embodiments described herein utilize progeny phage and/or bacteria labeled with a detectable moiety to facilitate detection of infected bacteria. For example, the progeny phage may comprise a gene that encodes a detectable biomolecule such as luciferase protein. In an alternative embodiment, the progeny phage may be quantified via infection of indicator bacteria comprising a marker biomolecule such as luciferase protein (e.g., bacteria that comprise a plasmid that encodes such a marker biomolecule may be used).

The use of indicator bacteria to assay sample cells via detection of lysed indicator cells progeny phage is depicted in FIG. 11. Thus, in this assay, parental phage used to infect a bacterial sample of interest are separated from progeny phage, and then the progeny phage are used to infect indicator bacteria engineered to express a biomolecule that provides a detectable signal upon lysis of the bacteria. For example, bacteria may be engineered by transfection with a plasmid that encodes a luciferase protein.

For example, in these experiments, a culture of indicator cells 401 (e.g., bacteria expressing luciferase protein) is grown. In the meantime, at least part of the sample comprising the bacteria to be quantified 400 is spin filtered to remove the media and an appropriate multiplicity of biotinylated phage 406 (e.g., T4 phage) added (excess phage 406 may be removed by centrifugation washing) and allowed to incubate long enough to infect and subsequently lyse the bacteria to release progeny phage. The resulting lysate 411 may then be collected, e.g., by centrifugation, and the filtrate 410 containing progeny phage and biotinylated parental phage transferred to a support 412 comprising streptavidin 414 (e.g., streptavidin columns) to separate the remaining biotinylated parent phage from the progeny phage 416 which are not biotinylated. Next the indicator cells 401 that produce a detectable moiety 403 (i.e., bacteria expressing luciferase protein) are added to the progeny phage 416 and the progeny phage are allowed to infect the bacteria. The infected indicator cells may incubated for a time sufficient for generation of additional phage and lysis to occur. The level of detectable moiety 403 (e.g., luciferase) released from the infected indicator bacteria may then be quantified using a luminometer 418 or other appropriate detection methods (e.g., fluorimeter for a fluorescent protein).

Figure 12A:
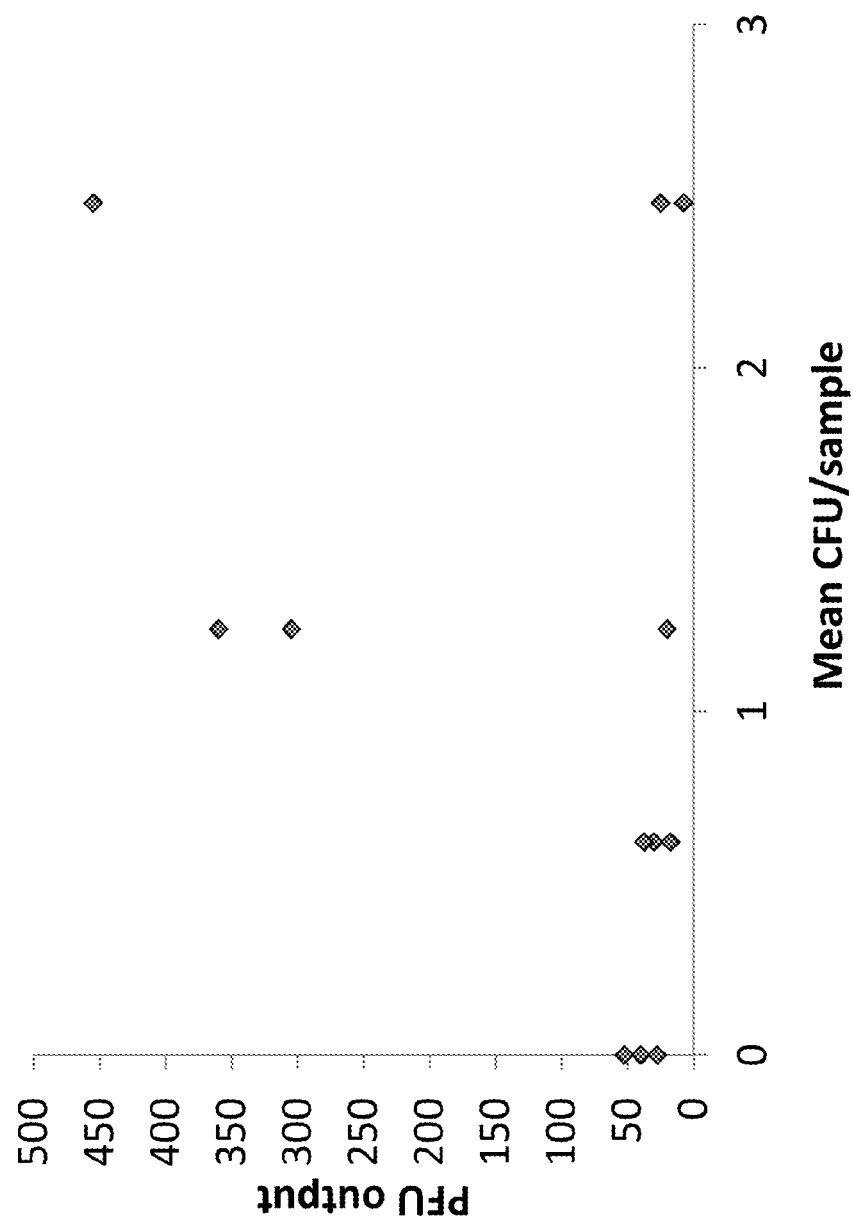
FIG. 12 panels A-C, shows the use of progeny phage detection from a bacterial sample of interest in accordance with alternate embodiments of the invention, where panel A shows detection of one or two bacterial cells using progeny phage, compared to a standard bacterial colony forming unit (CFU) assay; panel B shows dose response effect with the phage detection (PFU) assay of the invention, also as compared to a standard bacterial colony forming (CFU) assay; panel C shows detection of lysed indicator cells from phage that are the equivalent of progeny from a single bacterial cell (i.e., 100 phage) or 27 bacterial cells (i.e., 2700 phage); panel D shows the detection of 1, 5 and 7 sample bacterial cells per sample using the phage assay with indicator bacterial cells; and panel E shows the detection of high numbers (up to 10,000 cells) of sample bacterial cells per sample using the phage assay with bacterial indicator cells.
Figure 12C:
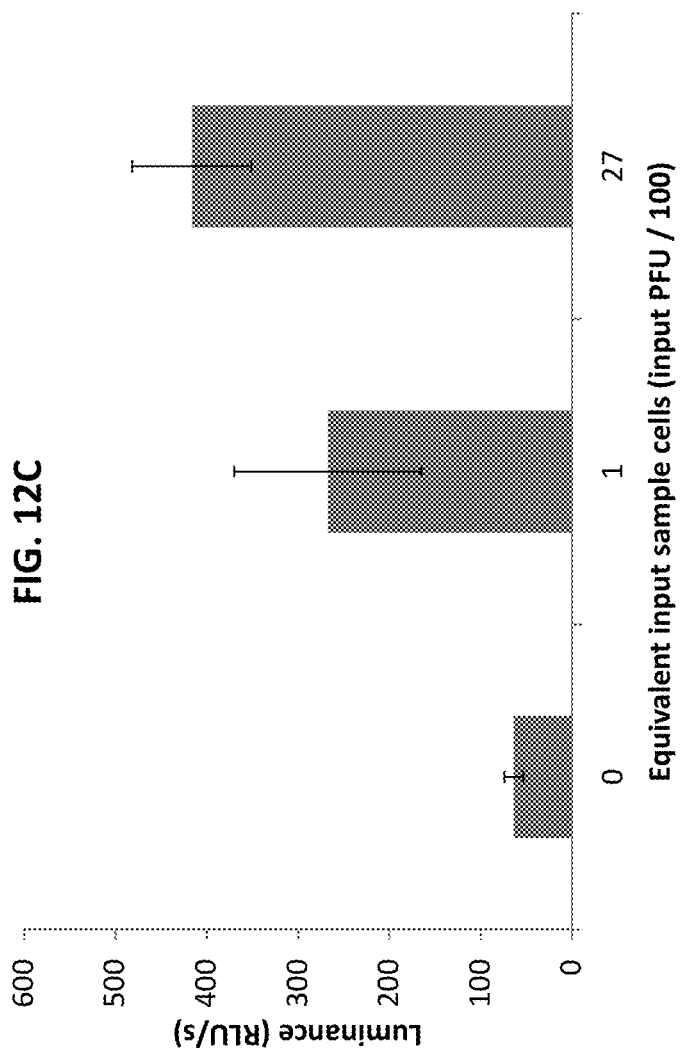

Data from example experiments using this assay are shown in FIGS. 12A-E. FIGS. 12A-C show separate data from the first and second halves of the method depicted in FIG. 11.

Figure 12D:
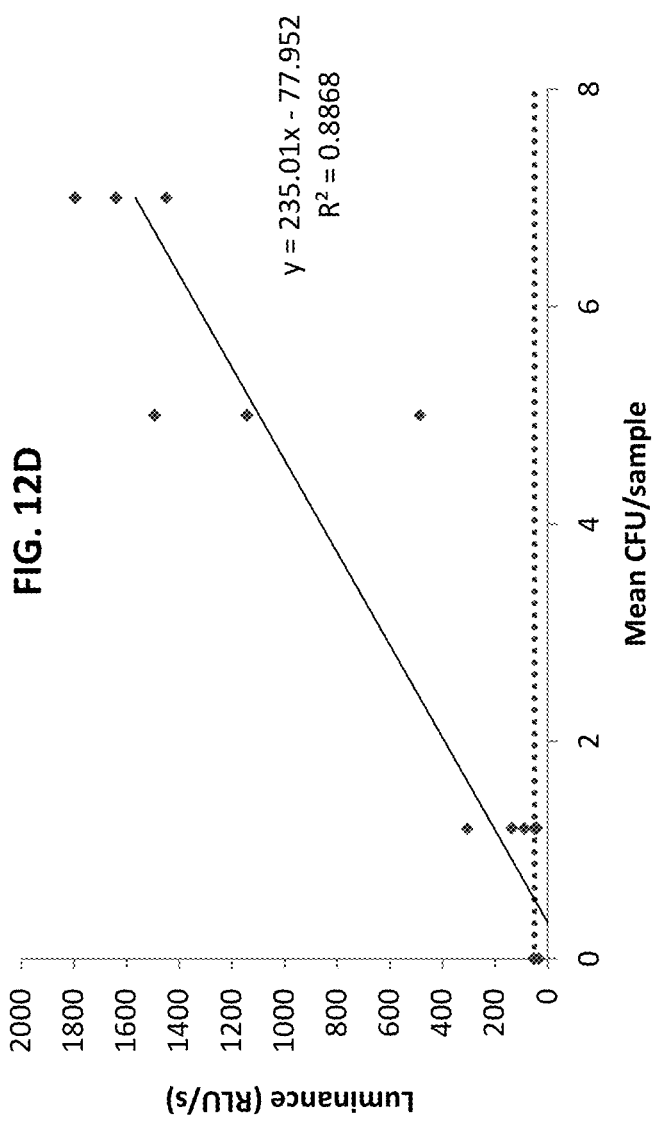

FIGS. 12D and 12E show data from the full assay.

FIG. 12A shows that as little as 1-2 *E. coli* cells can provide a measurable Plaque Forming Unit (PFU) concentration (i.e., about 300-460 PFU) of progeny phage via plaque assay. The points near 0 PFU (up to about 60 PFU) on the y-axis are likely due to no cells being deposited on the filter by random chance as an average of 1 cell per sample is likely to actually have 0 cells.

FIG. 12B shows that the phage assay demonstrates a dose dependent response to the input sample cells, increasing in progeny phage production the more cells in the sample. Both FIGS. 12A and 12B are plotted against cell concentrations determined from the standard overnight colony forming unit (CFU) assay, thus demonstrating similar sensitivity, at the inherently faster speed of a plaque assay which can be visualized in under 8 hours.

FIG. 12C shows detection of phage that are the equivalent of a single cell (i.e., 100 phage) or 27 cells (i.e., 2700 phage) using the second half of the method using lysis of indicator cells outlined in FIG. 11. This demonstrates, when combined, the full phage assay should be able to detect as few as 1 cell per sample.

FIG. 12D shows the detection of 1, 5 and 7 sample cells (e.g., *E. coli*), compared to a standard CFU assay (dotted line denotes background level). FIG. 12E shows the successful detection of 100 to 10,000 bacterial cells (determined microscopically) per sample using the full phage assay (line denotes background level). Thus demonstrating sensitivity from 1 to 10,000 cells with no dilution of the sample. This is 1 or 2 orders of magnitude more sensitive than a standard overnight CFU assay, where more than 500-700 CFU cannot be reliably counted on a Petri dish, in addition to being a much faster assay, performed in approximately 3 hours.

Also, in some embodiments, the assay may comprise detection of ribosomes released from indicator bacteria. In this format, the assay may then take advantage of the amplification provided by the progeny phage, as well as the amplification provided by the large numbers of ribosomes present in a single bacterial cell.

Figure 13:
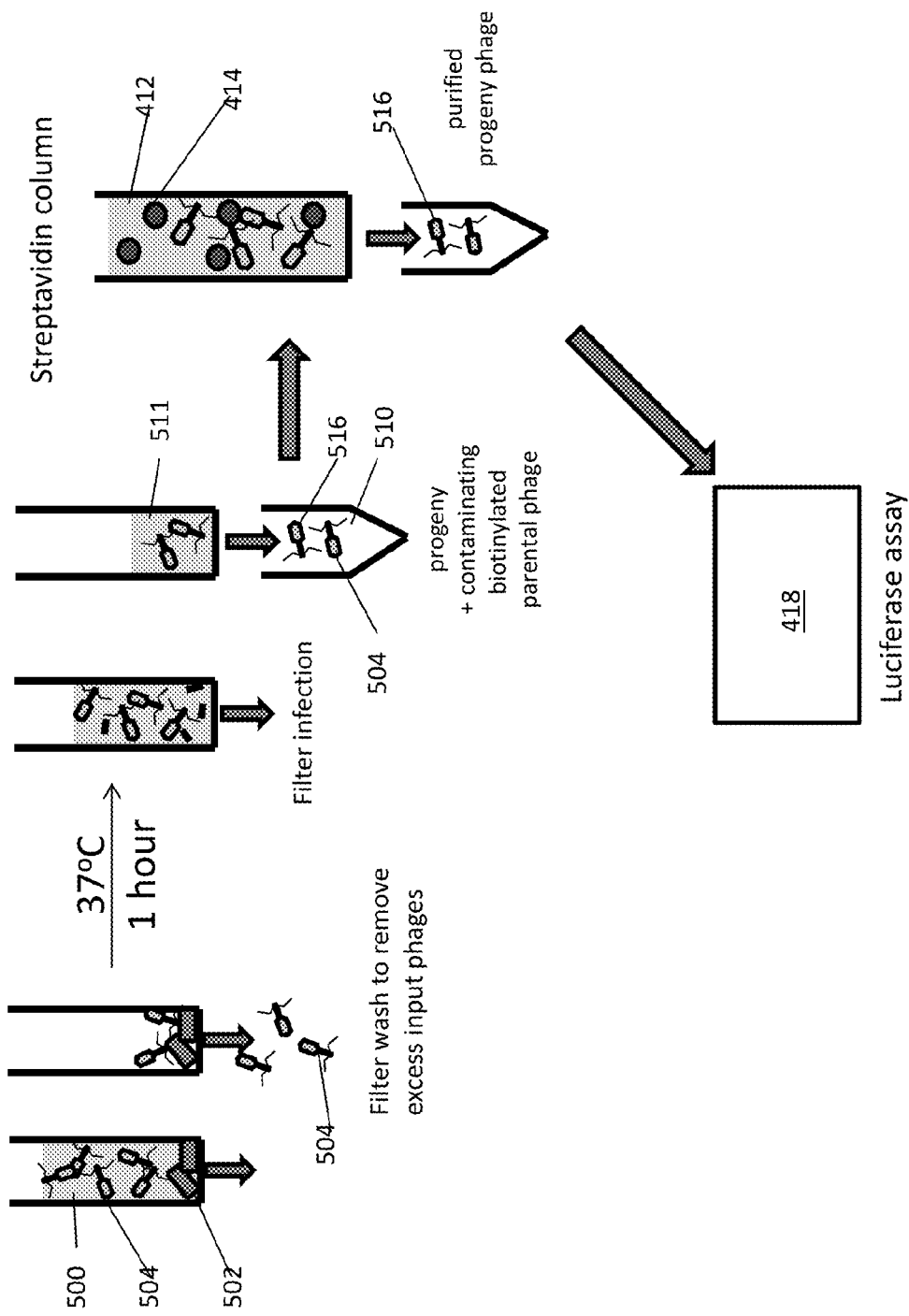
FIG. 13 depicts the use of indicator phage with capsid protein fused with luciferase to detect progeny phage isolated from bacterial cells in accordance with an embodiment of the invention.

The strategy of using indicator phage is shown in FIG. 13. In this method, a phage capsid protein is transgenically fused with luciferase such that progeny particles separated from biotinylated parental input phage on the streptavidin column contain luciferase (or other detection moiety) and can be directly quantified.

As illustrated in FIG. 13, in this method at least part of the sample 500 comprising the bacteria to be quantified 502 is spin filtered to remove the media and an appropriate multiplicity of biotinylated phage 504 (e.g., T4 phage) having a capsid protein fused with luciferase (indicator phage) added (excess phage 504 may be removed by centrifugation washing) and the remaining parental phage allowed to incubate long enough to infect and lyse the bacteria 511 to release progeny phage. The resulting lysate 510 may then be collected, e.g., by centrifugation, and the filtrate containing progeny phage and parental phage transferred to a support 412 comprising streptavidin 414 (e.g., streptavidin column) to separate the biotinylated parental phage from the progeny phage 516 which are not biotinylated. The level of luciferase present and active as a fusion protein with Soc capsid protein on the indicator progeny phage 516 may then be quantified using a luminometer 418. For example, about 100-200 progeny phage per cell, each comprising about 900 luciferase-capsid protein copies, yields about 200,000 luciferase copies.

The strategy of using indicator phage that produce soluble luciferase is shown in FIG. 14. In this method, the phage (e.g., T4 phage) are engineered to express a soluble luciferase during replication instead of a capsid protein-luciferase fusion. Expression of luciferase is driven by a viral capsid promoter (e.g., the Soc promoter in T4 bacteriophage), yielding high expression. Parental phage will be free of luciferase, so any luciferase detected in the assay must come from replication of progeny phage released from the bacterial cells. Thus, there is no need to separate out the parental phage and the progeny phage.

In these experiments, at least part of the sample 600 comprising the bacteria 602 to be quantified is spin filtered to remove the media and an appropriate multiplicity of biotinylated T4 phage that express luciferase instead of Soc capsid protein 604 are added. The parental 604 and progeny phage 616 in the filtrate from the infected bacteria 611 may then be collected, e.g., by centrifugation and the level of luciferase quantified using a luminometer 418.

Thus, in certain embodiments, the present invention utilizes both the high specificity provided by infectious agents and the amplification provided by replication of infectious agents as a means to detect low levels of a microorganism present in a sample. For example, in one embodiment, the present invention comprises methods and systems that utilize the specificity of bacteriophages for the isolation of bacteria from a sample and/or the amplification provided by progeny bacteriophage for the detection of a bacterium in a sample. For example, identification of the protein constituents (e.g., the lytic phage T4 of *Escherichia coli* has about 2500 protein subunits) of 200 progeny phage from each infected cell can yield a large amplification over methods dependent on the isolation and identification of a single cultivable cell.

Thus embodiments of the present invention include the use of an ultrasensitive bacteriophage-based assay for the rapid detection and quantification of bacterial pathogens. For example, the method may comprise the steps of: concentrating the bacteria from a sample on a bacteriological filter (e.g., 0.45 μm pore size); infecting the bacterium with biotinylated bacteriophage; washing unadsorbed input phage through the filter; incubating the infected cell for bacteriophage replication and cell lysis; and removing remaining input biotinylated phage from the lysate by the use of streptavidin purification (e.g., a spin column or other solid support).

Efficient removal of unadsorbed input phage can be integral to quantifying phage progeny. Inability to remove or selectively inactivate unadsorbed input bacteriophage can obviate quantification of progeny particles, and this has been a major impediment in bacteriophage-based bacterial detection methods. The progeny bacteriophage in the sample may be quantified by plating and plaque count (PFU assay), or by the use of indicator bacteria or indicator phage or the high gain amplification immunoassay described herein. The presence of progeny bacteriophage indicates the presence of a bacterial cell specific for the bacteriophage in the sample and the absence of progeny bacteriophage indicates the absence of a bacterial cell specific for the bacteriophage in the sample.

In another embodiment, the method may include contacting the sample with infectious agents that are bound to a solid support or other binding agent (e.g., biotinylated bacteriophage that are bound to a streptavidin-coated magnetic bead), wherein the bacteriophage are specific to the bacterial cell; incubating the sample under conditions effective for the bacteriophage immobilized on the solid support to infect the bacterial cell; isolating the infected cell-bacteriophage-solid support complex; incubating for phage replication and cell lysis, which results in the release of progeny phage which do not bind to the solid support and thus can be distinguished from the input immobilized phage used to infect the bacterium; removing the solid support with attached excess input bacteriophage and bacteriophage-cell envelope complexes; passing the lysate through a streptavidin spin column to eliminate any remaining input biotinylated phage; and quantifying the progeny phage by methods described herein. Again, the presence of progeny bacteriophage indicates the presence of a bacterial cell specific for the bacteriophage in the sample and the absence of progeny bacteriophage indicates the absence of a bacterial cell specific for the bacteriophage in the sample.

For the detection of a given bacterial cell, bacteriophage that are capable of infecting the bacterial cell, replicating within the bacterial cell and lysing the bacterial cell may be selected. For any given bacterial cell a wide variety of bacteriophage are available, for example, from ATCC (about 500 phage) or by isolation from natural sources that harbor the host cells. The bacteriophage should also exhibit specificity for the bacterial cell. A bacteriophage is specific for a bacterial cell when it infects the given bacterial cell and does not infect bacterial cells of other species or strains. For the detection of a particular bacterial cell, one would also preferably select bacteriophage that give an optimal or maximal burst size.

Where a bacteriophage is used either for isolation of the bacteria, and/or amplification of detection of the bacteria, the range of bacterial cells that can be detected by the present invention is limited only by the availability of a bacteriophage specific for the bacterial cell and will be realized to be vast by those skilled in the art. For example a list of phage types available from ATCC is published by them as the Catalogue of Bacteria & Bacteriophages and is available on the worldwide web at atcc.org. Other such depositories also publish equivalent data in their catalogues, and this may be used to identify possible bacteriophage reagents for the methods of the present invention.

The total reaction time for phage infection of a bacterium, phage multiplication or amplification in the bacterium, through lysing of the bacterium, may take anywhere from tens of minutes to hours, depending on the phage and bacterium in question and the environmental conditions. Once the bacterium is lysed, progeny phage are released into the environment along with all the contents of the bacterium. The progeny phage can infect other bacteria that are present, and repeat the cycle to create more phage and more bacterial debris. In this manner, the number of phage will increase exponentially until there are essentially no more bacteria to infect.

Bacteriophage have the capability to exhibit specificity in addition to the ability to produce a substantial amount of progeny in a short period of time. And, bacteriophage replication denotes a living host cell. Under optimum infection and host growth medium conditions, a given phage/bacterium combination gives rise to a consistent number of phage progeny. Generally, the lytic infection cycle produces 100 or more progeny phage particles from a single infected cell in about one-half hour to one hour. Within an assay it may be necessary to include control comparison standards, done in the same medium, with known numbers of phage infecting known numbers of substrate-bound target cells.

Other Detection Assays

The presence of progeny bacteriophage and/or ribosomes isolated from a microorganism may also be determined by other methods well known in the art. For example, progeny bacteriophage may be detected by conventional plaque assay methods or by automated technologies, including, for example, cell sorters, such as fluorescent activated cell sorting (FACS).

Progeny bacteriophage may also be detected by direct visualization (Anderson et al., (US 2004/0137430, the disclosure of which is incorporated by reference herein). Such direct visualization may utilize light or fluorescence microscopy. Stains or enzymes that may be used include, but are not limited to, the fluorescent probe Alexa Fluor (available from Life Technologies/Molecular Probes, Grand Island, N.Y.), Cy3, fluorescein isothiocyanate, tetramethylrhodamine, horseradish peroxidase, alkaline phosphatase, glucose oxidase or any other label known in the art. Alternatively a laser system may be used to detect labeled bacteriophage. Other detection methods include the detection of adenylate kinase, see Murphy et al., pp. 320-322 of Bioluminescence and Chemiluminesence in Medicine and Disease, Clinical Chemistry and Microbiology, and detection using a binomial-based bacterial ice nucleation detection assay, see Irwin et al., Journal of AOAC International 83:1087-95 (2000). Or, for some embodiments, progeny bacteriophage may also be detected by methods utilizing bioluminescence, detecting the expression of a luciferase gene cloned into the bacteriophage genome as outlined in FIGS. 12 and 13, or incorporated in an indicator bacteria as indicated in FIG. 11. See, for example, Loessner et al., Applied and Environmental Microbiology 62(4):1133-1140 (1996).

Also, QUANTUM DOTS (also referred to herein as "QDOTS®") nanocrystals, manufactured by Life Technologies/Molecular Probes may be used in the methods of the present invention to detect immunocomplexes, e.g., as for detection of ribosomal proteins or phage proteins released from bacterial cells. QDOTS® are nanoscale crystals that exhibit a number of favorable characteristics over conventional fluorescent dyes. Unlike fluorescent dyes, QDOTS® nanocrystals photobleach much more slowly and fluoresce much more brightly. Because of the array of different sizes available, QDOTS® nanocrystals cover a broader optical spectrum (i.e., different sizes emit different colors), thereby allowing for the detection of different organisms in the same sample. QDOTS® nanocrystals are manufactured with the same uniform conjugational chemistry, thereby providing consistent behavior under multiple assay environments. Currently, QDOTS® nanocrystals are available as several different conjugates, including streptavidin, protein A, and biotin. In some embodiments of the present invention, streptavidin conjugates may be used to fluoresce progeny bacteriophage or ribosomes or their constituent proteins via a QDOTS®-streptavidin-biotin-antibody complex, or QDOTS® can be directly conjugated to antibodies. The streptavidin conjugates are extremely bright, provide excellent photostability, and have a single excitation source.

Samples

Each of the embodiments of the methods and systems of the invention can allow for the rapid detection and quantification of microbes in a sample. For example, certain of the methods according to the present invention can be performed, most preferably, in about two hours or less.

Microbes detected by the methods and systems of the present invention include pathogens that are of commercial, medical or veterinary concern. Such pathogens include Gram-negative bacteria, Gram-positive bacteria, *mycoplasma* and viruses (proteins of viruses only, as viruses do not have ribosomes). Any microbe for which a binding agent that is specific for the particular microbe has been identified can be detected by the methods of the present invention. Those skilled in the art will appreciate that there is no limit to the application of the present methods other than the availability of the necessary specific binding agent/microbe pairs.

Bacterial cells detectable by the present invention include, but are not limited to, bacterial cells that are food or water borne pathogens. Bacterial cells detectable by the present invention include, but are not limited to, all species of *Salmonella*, all species of *Escherichia coli*, including, but not limited to *E. coli* 0157/H7, all species of *Listeria*, including, but not limited to *L. monocytogenes*, and all species of *Campylobacter*. Bacterial cells detectable by the present invention include, but are not limited to, bacterial cells that are pathogens of medical or veterinary significance. Such pathogens include, but are not limited to, *Bacillus* spp., *Bordetella pertussis, Camplyobacter jejuni, Chlamydia pneumoniae, Clostridium perfringens, Enterobacter* spp., *Klebsiella pneumoniae, Mycoplasma pneumoniae, Salmonella typhi, Shigella sonnei, Staphylococcus aureus*, and *Streptococcus* spp.

The sample may be environmental or food or water samples and medical or veterinary samples. Samples may be liquid, solid, or semi-solid. Samples may be swabs of solid surfaces. Samples may include environmental materials, such as the water samples, or the filters from air samples or aerosol samples from cyclone collectors. Samples may be of meat, poultry, processed foods, milk, cheese, or other dairy products. Medical or veterinary samples include, but are not limited to, blood, sputum, cerebrospinal fluid, and fecal samples and different types of swabs.

Samples may be used directly in the detection methods of the present invention, without preparation or dilution. For example, liquid samples, including but not limited to, milk and juices, may be assayed directly. Samples may be diluted or suspended in solution, which may include, but is not limited to, a buffered solution or a bacterial culture medium. A sample that is a solid or semi-solid may be suspended in a liquid by mincing, mixing or macerating the solid in the liquid. A sample should be maintained within a pH range that promotes bacteriophage attachment to the host bacterial cell. A sample should also contain the appropriate concentrations of divalent and monovalent cations, including but not limited to $Na^+$, $Mg^{2+}$, and $K^+$. Preferably a sample is maintained at a temperature that maintains the viability of any pathogen cells contained within the sample.

Preferably throughout detection assays, the sample is maintained at a temperature that maintains the viability of any pathogen cell present in the sample. During steps in which bacteriophages are attaching to bacterial cells, it is preferable to maintain the sample at a temperature that facilitates bacteriophage attachment. During steps in which bacteriophage are replicating within an infected bacterial cell or lysing such an infected cell, it is preferable to maintain the sample at a temperature that promotes bacteriophage replication and lysis of the host. Such temperatures are at least about 25 degrees Celsius (C), more preferably no greater than about 45 degrees C., most preferably about 37 degrees C. It is also preferred that the samples be subjected to gentle mixing or shaking during bacteriophage attachment, replication and cell lysis. In other embodiments, the phage assembly may be inhibited after infection such that the subunits of the phage proteins accumulate unassembled and can provide an additional amplification of the progeny phage.

Assays may include various appropriate control samples. For example, control samples containing no bacteriophage or control samples containing bacteriophage without bacteria may be assayed as controls for background levels.

Substrates

Substrates to be used in the methods include, but are not limited to, plain polystyrene or magnetic beads (Spherotech, Libertyville, Ill.; Life Technologies/Invitrogen, Grand Island, N.Y.; Polyscience, Niles, Fla.; Thermo Scientific Pierce, Waltham Mass.; EMD Millipore, Billerica, Mass.; New England Biolabs, Ipswich, Mass.), and plain or magnetic silica beads (AmsBio, Lake Forest, Calif.), latex coatings, a membrane filter, a fiber filter, a free fiber or a porous solid substrate. Methods for the use of magnetic beads can be found, for example, with the package insert of Dynabeads Protein G Prod. No. 10003D, in Kala et al., Analytical Biochemistry 254:263-266 (1997) and in Dutton, Genetic Engineering News, Volume 22 (13), July 2002.

A wide spectrum of particles, particularly magnetic and polystyrene beads, are commercially available in a wide range of sizes. For certain embodiments, a preferred set of particles has an average particle diameter of about one micrometer (i.e., one micron). For certain embodiments, in particular in agglutination assays, a preferred set of particles has an average particle size (i.e., the largest dimension of the particles) of no greater than twenty micrometers (i.e., microns).

For certain embodiments, e.g., retrieval of microorganisms, ribosomes, bacteriophage or their constituents, the particle (e.g., beads) concentration is preferably at least $10^8$ per milliliter. For certain embodiments, the concentration of particles (e.g., beads) is preferably no greater than $10^9$ per milliliter.

For certain embodiments, e.g., particle clumping by ribosomes, bacteriophage or their constituents, the number of particles (e.g., beads) is preferably at least 300 particles and no greater than 3,000 particles (e.g., beads) in 10 to 20 µl. In embodiments involving visualization of microorganisms or viruses attached to beads, this particle number (e.g., beads) allows for light microscopic evaluation in a two-dimensional array without stacking.

Exemplary commercially available plain or magnetic beads include polystyrene beads coated with protein G, protein A, proteins A/G, epoxy, or streptavidin, all available from Invitrogen, Grand Island, N.Y., or from Spherotech, Libertyville, Ill. MagSi, magnetic silica beads with these same coatings, are available from AmsBio, Lake Forest, Calif.

Systems for Detection of Microorganisms

Embodiments of the invention also comprise systems (e.g., kits) for performing the methods of the invention.

For example, in an embodiment, the invention comprises a kit comprising components for detecting a microorganism of interest comprising: a component for isolating the microorganism from other components in the sample; a component for lysing the microorganism to release ribosomes present in the microorganism; and a component for detecting the ribosomes, or a constituent of the ribosomes, wherein detection of the ribosomes or a constituent of the ribosomes, indicates that the microorganism is present in the sample.

A variety of microorganisms may be detected using the kits of the invention. In an embodiment, the microorganism comprises at least one of a bacterium, or a fungus, or yeast.

In an embodiment, the component isolating the microorganism comprises a binding agent that recognizes binds to the microorganism. The binding agent may be bound to a solid support. In an embodiment, the binding agent may be an antibody. Or, where the microorganism is a bacterium, the binding agent may be a bacteriophage specific for the bacterium.

In an embodiment, the kit may comprise a primary antibody that recognizes the ribosomes, and at least one secondary antibody that recognizes the primary antibody. Or, the kit may comprise a primary antibody that recognizes the ribosomes, and at least one second primary antibody that recognizes the ribosomes. In certain embodiments, the second primary antibody is bound to a solid support. In yet other embodiments, the solid support comprises a plurality of second primary antibodies.

In other embodiments, the ribosomes may be detected using a lateral flow assay. For example, in one embodiment, kit may comprise a solid support comprising anti-ribosome antibodies. In an embodiment, the kit may comprise at least one carbon black nano-string comprising additional anti-ribosome antibodies.

In another embodiment, the invention comprises a kit comprising components for detecting a microorganism of interest comprising: a component for isolating at least one microorganism from other components in the sample; a component for infecting the at least one microorganism with a plurality of a parental infectious agent; a component for lysing the at least one infected microorganism to release progeny infectious agents present in the microorganism; and a component for detecting the progeny infectious agents, or a constituent of the progeny infectious agents, wherein detection of the infectious agent or a constituent of the infectious agent, indicates that the microorganism is present in the sample. In an embodiment, the microorganism is a bacterium and the infectious agent is a bacteriophage.

The kits may comprise a variety of components for detection of progeny infectious agents. For example, in an embodiment, the progeny infectious agent (e.g., bacteriophage) may comprise an indicator moiety. In an embodiment, the indicator moiety in the progeny infectious agent may comprise luciferase fused to a structural protein (e.g., a phage capsid protein). In an embodiment, the indicator moiety in the progeny infectious agent (e.g., bacteriophage) may be a detectable moiety that is expressed during replication, such as a soluble luciferase protein. In an alternate embodiment, the kit may comprise indicator microorganism (e.g. bacteria) that comprise a protein that is released upon lysis of the indicator microorganism when infected with progeny infectious agents. In an embodiment, the protein release from the indicator microorganism may comprise a detectable moiety. For example, in an embodiment, the protein released is a luciferase protein. In an alternate embodiment, the kit may comprise components such that progeny infectious agent from infected samples cells and/or indicator cells may be detected by lateral flow assay with carbon black nanostrings. Or, the protein released from the indicator microorganism may comprise ribosomes. In this way, the kit combines the amplification provided by bacteriophage infection with the amplification provided by ribosome detection.

Kits for Isolation of Microorganisms from a Sample

Kits of the invention may comprise reagents for isolation of bacteria from a sample.

For example, in certain embodiments, the kit may comprise an antibody specific to the microorganism of interest. The antibody may, in certain embodiments, comprise a first binding agent that can be recognized by a second binding agent such that microorganism may be isolated by the interaction of the binding agents. For example, in certain embodiments, the kit may comprise biotinylated antibodies that recognize a microorganism of interest and streptavidin-coated beads.

In alternate embodiments, the kit may comprise a specific phage that can be linked to an immobilized binding agent such as, but not limited to: streptavidin; biotin; an antibody that specifically binds to the bacteriophage or to a bacteriophage substructure, such as the head. In an embodiment, the agent linked to the bacteriophage is used to link the phage to a solid support. For example, in one embodiment, the kit may comprise a biotinylated phage specific for a bacterium of interest. In this way, the biotinylated phage can be bound to a streptavidin magnetic bead. In alternate embodiments, bacteriophages, phages, mycobacteriophages (such as for TB and paraTB), mycophages (such as for fungi), *mycoplasma* phages, and any other virus that can invade living bacteria, fungi, *mycoplasma*, protozoa, yeasts, and other microscopic living organisms can be coupled to a solid support for isolation of a microbe of interest. As an example, well-studied phages of *E. coli* include T1, T2, T3, T4, T5, T7, and lambda; other *E. coli* phages available in ATCC collection include phiX174, S13, Ox6, MS2, phiV1, fd, PR772, and ZIK1.

Kits for Ribosome-Based Detection of Microorganism

In certain embodiments, the kits may comprise reagents for detection of ribosomes and/or ribosomal proteins from a microbe of interest. For example, in one embodiment, the kit may comprise polyclonal antisera produced in rabbits, mice, guinea pigs or the like, for example, against purified ribosomes of *E. coli* or *Salmonella* spp or a mammalian cell.

An LFA kit for the detection of ribosomal proteins may include sample strips containing the appropriate antibodies at both test and control lines. Such kits may also include carbon black nano-strings bound to antibodies specific for the analyte of interest. The kit may also include a running buffer and/or any reagents required for dilution of the sample or other reagents. Additional reagents may include material to serve as controls and reagents for further signal amplification. For example, the kit may include a secondary CBNS-Ab (i.e., a secondary antibody that recognizes the primary antibody to the analyte of interest). The kit may also include enzymatic detection reagents such as horse radish peroxidase (HRP) and/or HRP substrates. An appropriately sized reservoir for running the assay may also be included in kits of the invention.

Kits for Phage-Based Detection of Microorganisms

For phage-based detection techniques, any of the commercially available phage may be used to generate reagents for the kits of the invention. For example a list of phage types available from ATCC is published by them as the Catalogue of Bacteria & Bacteriophages and is available on the worldwide web at atcc.org or other known depositories.

Bacteriophage may be immobilized on a substrate by one of many procedures known in the art. For example, an antibody specific for the bacteriophage may be used to attach a bacteriophage to a substrate. Protein A, protein G, or ligands such as avidin, streptavidin and biotin, may be used to link the antibody to the substrate. Covalent linkage methods may also be used to attach a bacteriophage to a substrate. Generally, antibodies with specificity for bacteriophage tail proteins should not be used, as the binding of such an antibody to the tail proteins can interfere with the ability of the bacteriophage particles to bind to a host bacterial cell.

The kits of the invention may comprise bacteria comprising detection moieties. Such bacteria are termed "Indicator Bacteria" may be composed of bacterial strains also susceptible to the same bacteriophage as the sample bacteria to be detected. For example, wild type *E. coli* strain B (ATCC), may be modified to express luciferase, or some other detection moiety, from a DNA plasmid. Plasmids may be constructed de novo or based on commercially available constructs, such as luciferase plasmids, pGL.4.10 (Firefly luciferase) (Promega, Madison Wis.) and pGL.4.70 (Renilla luciferase). The addition of a constitutive or viral promoter to drive expression of the detection moiety (e.g. luciferase) may be included, along with other common DNA sequences known in the art (antibiotic resistance gene and replication origin).

Additionally and/or alternatively, the kits of the invention may comprise "Indicator Phage". Indicator phage may consist of bacteriophage with their genomes modified to include genes for the expression of common detection moieties, such as luciferase, green fluorescent protein, or horseradish peroxidase. These genes may be integrated into a high copy number protein in a fusion, such as a Soc-luciferase fusion in T4, or as a soluble protein, not incorporated into the phage structure, but expressed upon phage infection of bacteria.

The kits may also comprise filters for use in concentrating and/or providing a substrate for bacteria to be infected by phage, then washed, such as 0.45 µm spin filters (Millipore, Billerica, Mass.). Streptavidin affinity columns may also be included in the kit, for use of separating biotinylated parental phage from progeny phage (GE Healthcare, Little Chalfont, UK). The kits may also contain substrates for use with detection moieties, such as D-luciferin or Luciferase Assay Substrate (Promega, Madison, Wis.) for Firefly luciferase, or coelenterazine for Renilla luciferase.

Also, an LFA kit for the detection of bacteriophage proteins may include sample strips containing the appropriate antibodies at both test and control lines. Such kits may also include carbon black nano-strings bound to antibodies specific for the analyte of interest. The kit may also include a running buffer and/or any reagents required for dilution of the sample or other reagents. Additional reagents may include material to serve as controls and reagents for further signal amplification. For example, the kit may include a secondary CBNS-Ab (i.e., a secondary antibody that recognizes the primary antibody to the analyte of interest). The kit may also include enzymatic detection reagents such as horse radish peroxidase (HRP) and/or HRP substrates. An appropriately sized reservoir for running the assay may also be included in kits of the invention.

Immunoassay Kits

In alternate embodiments, the kit may comprise reagents for a bead-based immunoassay. In an embodiment, the invention may comprise kit for assaying an analyte of interest comprising a detection support, the detection support comprising solid support comprising a plurality of binding agent molecules that can recognize and bind to the analyte of interest. In an embodiment, the kit may comprise a capture support, the capture support comprising at least one capture support binding agent that recognizes and binds to the analyte of interest. The kit may, in some embodiments, further comprise a binding agent that can specifically recognize and bind to the plurality of binding agent molecules on the detection support. In an embodiment, the binding agent that can specifically recognize and bind to the plurality of binding agent molecules on the detection support is a soluble binding agent.

The detection and/or capture supports may comprise a variety of formats. In an embodiment, the capture solid support may be an assay well (i.e., such as a microtiter plate). Or, the capture solid support may be a location on an array, or a mobile support, such as a bead. In an embodiment, the detection support is a mobile support such as bead.

A variety of binding agents may be used in the kits of the invention. For example, the plurality of binding agents attached to the detection support may be either antibodies or an antibody fragments that recognize the analyte of interest. Additionally and/or alternatively, the binding agent attached to the capture support may be an antibody or an antibody fragment that recognizes the analyte of interest. Additionally and/or alternatively, the binding agent that can specifically recognize and bind to the plurality of binding agent molecules on the detection support may be an antibody or an antibody fragment. In an embodiment, the binding agent that can specifically recognize and bind to the plurality of binding agent molecules on the detection support does not recognize the capture binding agent used to bind the analyte of interest to the capture solid support. Or, the binding agent on any of the capture or detection supports, or the binding agent that can specifically recognize and bind to the plurality of binding agent molecules on the detection support may comprise a protein that binds a non-protein target (i.e., such as a protein that specifically binds to a small molecule analyte of interest, or a receptor that binds to a protein).

The detection support may comprise a plurality of detectable moieties. Additionally and/or alternatively, the binding agent that can specifically recognize and bind to the plurality of binding agent molecules on the detection support may comprise a detectable moiety.

The use of a detection support comprising a plurality of binding agents that recognize the analyte of interest provides amplification of the signal. In alternate embodiments, the detection support comprises more than 1,000, or more than 10,000, or more than 100,000, or more than 500,000, or more than 1,000,000 binding agent molecules specific for the analyte of interest. Thus, in alternate embodiments, the kits of the invention provides an amplification that ranges from 1,000 to 1,000,000,000, or from 1,000 to 100,000,000, or from 5,000 to 10,000,000, or from 10,000 to 1,000,000, or from 10,000 to 500,000, or from 50,000 to 500,000 times the signal seen in a standard, unamplified immunoassay that does not comprise a detection support comprising a plurality of detection binding agents. Or, ranges within these ranges may be achieved.

Thus, in certain embodiments, the kit may comprise reagents for a bead-based immunoassay. Thus, in one embodiment, the detection support may comprise a bead coated with an antibody that recognizes a protein of interest. The bead may in certain embodiments be a polystyrene bead coated with proteins G, protein A, or proteins A/G, which are available commercially (e.g., Invitrogen, Carlsbad Calif.) in a wide variety of sizes. Other beads that may be useful include magnetic silica beads coated with these same proteins (MagSi beads from AmsBio, Lake Forest, Calif.)

Thus, in one embodiment, the kit may comprise a bead coated with an antibody that recognizes a ribosomal protein. Or, the kit may comprise a bead coated with an antibody that recognizes a phage protein. The beads may be polystyrene, silica, glass, or other, plane or derivatized for attachment to specific chemical groups.

Substrates to be used in the kits of the present invention include, but are not limited to, polystyrene beads (Spherotech, Libertyville, Ill.), magnetic beads (Invitrogen; AmsBio), latex coatings, a membrane filter, a fiber filter, a free fiber or a porous solid substrate. Methods for the use of magnetic beads can be found, for example, with the package insert of Dynabeads Protein G Prod. No. 10003D, in Kala et al., Analytical Biochemistry 254:263-266 (1997) and in Dutton, Genetic Engineering News, Volume 22, Number 13, July 2002.

A wide spectrum of particles, particularly magnetic and polystyrene beads, is commercially available in a wide range of sizes. For certain embodiments, a preferred set of particles has an average particle size (i.e., the largest dimension of the particles) of about one micrometer (i.e., micron). For certain embodiments, a preferred set of particles has an average particle size (i.e., the largest dimension of the particles) of no less than 10 micrometers (i.e., microns). Exemplary commercially available beads are protein G-, protein A-, and proteins A/G-coated polystyrene beads and streptavidin-coated polystyrene beads that are available from Invitrogen, Carlsbad, Calif. or from Spherotech, Libertyville, Ill. Other suppliers of polystyrene and magnetic beads include Thermo Scientific Pierce, Millipore, Polyscience and New England Biolabs. AmsBio, Lake Forest, Ill. is a supplier of magnetic silica beads, which are available with all of the protein coatings given above. Life Technologies/Invitrogen also supplies epoxy surface magnetic beads, which bind antibodies covalently.

The number of antibody molecules on the beads may vary. In alternate embodiments, there may be about 10,000 to 10,000,000 or about 50,000 to 1,000,000, or about 100,000 to 500,000 antibodies for a bead that is about 15 μm in diameter. For beads of different sizes, corresponding surface coverage can be used.

In certain embodiments the beads are sufficiently large such that a plurality of the anti-ribosome antibodies may be attached to the bead. For example, the beads may range in size from about 0.1 to 50, or 0.2 to 40, or 0.5 to 30, or 1 to 20, or 1 to 15 or about 1 to 3 μm in diameter. To complex the antibody of interest to the bead, the bead may be precoated with protein G, protein A, proteins A/G, or another protein that complexes to the antibody of interest. Such beads are generally available commercially. The kits for a bead-based immunoassay may also comprise additional primary antibodies for the protein of interest, where such antibodies are from a second species. These antibodies are used in sandwich assays described herein because they bind secondary antibody-reporter complexes, and the secondary complexes do not bind to first-species antibodies on the solid surface, which would result in false positive reactions. However, the second-species antibodies may also be used to coat a solid surface and/or microtiter well as described herein.

The kits may also comprise secondary antibodies that can be used to detect the primary antibodies, where such antibodies may be anti-globulin antibodies from the second species. These antibodies may be labeled with a detectable marker or a binding agent that can complex with a detectable marker. For example, in certain embodiments, a kit of the invention may comprise a secondary antibody that is bound to a fluorophore. In an embodiment, the fluorophore may comprise a QDOT®. For example, in one embodiment, streptavidin-QDOTS® can be bound to biotinylated secondary antibodies that recognize, e.g., an anti-ribosome primary antibody.

EXAMPLES

Embodiments of the present invention may also be characterized by the following non-limiting examples.

Example 1

Purified Ribosome Isolation

E. coli was obtained from ATCC (#11303) and cultured in LB Medium (Difco: 10 g Tryptone, 5 g yeast extract, 10 g NaCl/L) overnight at 37° C. A colony was placed in 5 mL of LB Medium and incubated at 37° C. overnight. The following day the culture was diluted 1:100 in fresh LB and the cells grown to a concentration of Klett 68 (OD at 600 nm=0.8) (20 Klett units on a Summerson Photoelectric Colorimeter=0.1 OD at 540 nm on a spectrophotometer), which corresponds to approximately $4 \times 10^8$ cells/mL after growth for about 3.5 hours. The cells were then pelleted in a Beckman Coulter XL 80K Type 19 rotor (Cat. No. 325632) at 5,000 rpm for 15 minutes. The pellet was resuspended in 1 mL TMS (50 mM Tris-HCl, pH 7.8, 10 mM $MgCl_2$, 100 mM NaCl) with 1/10 volume of 10× Bugbuster (Novagen, PN 70921-3), 0.5 mg/ml lysozyme (Sigma L6876), and 10 μg/mL high quality DNaseI (RNase free) (USB 14365). The lysate was clarified in a 1.5 mL microfuge tube in a Beckman Coulter Allegra 64R F2402 rotor at 16,000 rpm for 10 min. The supernatant was transferred to a fresh microfuge tube and the clarification step repeated. Ribosomes were pelleted in TMS by centrifugation at 35,000 rpm for 3 hours at 4° C. in a Beckman Coulter SW40Ti rotor and the pellet resuspended in 0.5 ml TMS. The suspension was clarified and loaded onto 10-30% (w/v) sucrose gradients in TMS (BioComp GradientMaster, BioComp, New Brunswick, Calif.) and spun at 35,000 rpm for 3 hours at 4° C. in a Beckman Coulter SW40Ti rotor. The resulting bands of ribosomes were removed by the use of a 21G×1" needle on a 3 mL syringe. The ribosomes were pelleted again as described above and the pellet resuspended in PBS or TMS. The ribosomal proteins were characterized by SDS-PAGE and purity of the particles confirmed by EM negative staining.

Example 2

Polyclonal Antibody Production in Rabbits

Purified ribosomes, isolated as described in Example 1, were combined with an appropriate adjuvant. The ribosomes and adjuvant were injected beneath the skin of young rabbits (2.5-3.0 kg; 10-16 weeks of age). Blood was collected from the central ear artery with a 19-gauge needle and allowed to clot and retract at 37° C. overnight. The clotted blood was then refrigerated for 24 hours before the serum was decanted and clarified by centrifugation at 2500 rpm for 20 minutes. The rabbits were injected and bled according to the following schedule:

Day −4: Pre Bleed
Day 0: Immunize via an intradermal (ID) route using CFA (Complete Freund's Adjuvant)
Day 7: Booster injection via an intradermal (ID) route using IFA (Incomplete Freund's Adjuvant)
Day 14: Booster injection via a subcutaneous (SC) route using IFA
Day 28: Booster injection via a subcutaneous (SC) route using IFA
Day 38: Test Bleed
Day 40: Ship pre-immune bleeds and test bleeds to NGI
Day 45: Terminal Bleed (approved)
Day 47: Ship terminal bleed to NGI
Day 49: End of project (approved)

Example 3

Bacteria Capture from Solution Using Cell-Specific Antibodies and Magnetic Microparticles In order to demonstrate capturing intact, viable bacterial cells from solution rabbit polyclonal antibodies to surface epitopes of various bacterial species (e.g., *E. coli* and *S. typhimurium*) were generated.

Cultures of both *E. coli* and *S. typhimurium* were grown in liquid media before harvesting and were washed with phosphate buffer (1.1 mM $KH_2PO_4$, 5.6 mM $Na_2HPO_4$, 154 mM NaCl, pH 7.4). The washed cells were then diluted to a concentration between 5-20 cells per ml. Approximately 250 ng biotinylated, polyclonal anti-*E. coli* antibody (equivalent to about $1\times10^{12}$ antibody molecules) produced by Rockland Immunochemicals Inc., Gilbertsville, Pa. was added to the cell suspension and allowed to incubate for 45 min. A control experiment, where antibody is not added to the cell suspension, was also done.

Following antibody incubation, $4\times10^8$ streptavidin-coated magnetic microparticles (Solulink, Inc., San Diego, Calif.) were added to the mixture and incubated a further 15 min. The cell-antibody-bead complexes were then collected using a magnetic stand, and the unbound fraction (supernatant) removed and the beads were gently washed with phosphate buffer (1.1 mM $KH_2PO_4$, 5.6 mM $Na_2HPO_4$, 154 mM NaCl, pH 7.4). Both supernatant ("sup") and bead ("bead") fractions were then spread onto Luria-Bertani (LB) agar plates and incubated overnight at 37° C. Following overnight culture, the plates were inspected for colony formation. FIG. 2 depicts an example experiment; colony counts are shown below left/right of each plate.

FIGS. 3A and 3B shows ribosomal protein capture using biotinylated anti-ribosomal IgG and magnetic bead linked to streptavidin. FIG. 3A demonstrates that anti-ribosome antibodies and streptavidin beads are necessary and able to capture ribosomes from solution quantitatively. In the experiment shown as FIG. 3A, lysate from 100,000 cells in 0.6M guanidine thiocyanate/phosphate buffered saline with Tween-20 (1.1 mM $KH_2PO_4$, 5.6 mM $Na_2HPO_4$, 154 mM NaCl, 0.01% Tween-20, pH 7.4) were incubated for 1 hour with varying amount of rabbit biotinylated, anti-ribosome IgG produced by Rockland Immunochemicals Inc., Gilbertsville, Pa. A no lysate control was also included. Next, between $3.3\times10^7$ and $1\times10^8$ Streptavidin (SA) magnetic Dynabeads (Life Technologies, Carlsbad Calif.) were added to each reaction so that the ratio of antibodies to beads was constant at 6000 antibody molecules per bead particle. About $5\times10^7$ SA beads were added to the "no antibody" control.

The beads were collected using a magnetic stand and then were denatured by adding sodium dodecyl sulfate sample buffer containing beta-mercaptoethanol and boiling. The eluant was then collected using a magnetic stand, run on a polyacrylamide gel, and subjected to Western blot analysis using rabbit anti-ribosome antibody and anti-rabbit Horse Radish Peroxidase (HRP) secondary antibody. It can be seen that when no anti-ribosome antibody is added, the ribosomal proteins are not detected. It can also be seen that 50 ng antibody is capable of binding all the ribosomal proteins from 100,000 cells.

In FIG. 3A, the Ponceau row provides an internal control to show that sample was loaded in all of the wells as Ponceau is a total protein stain used to visualize proteins present on a Western blot membrane. The SA row shows the streptavidin removed from the SA Dynabeads during the denaturation/boiling step. It can be seen that approximately equal amounts of beads were used in each ribosome capture step.

FIG. 3B demonstrates that addition of biotin, anti-ribosome antibodies and streptavidin beads is sufficient for capturing all ribosomal proteins present in solution. In this experiment, lysate from 270,000 cells in 0.6 M guanidine thiocyanate/phosphate buffered saline with Tween-20 were incubated with or without 200 ng rabbit biotinylated, anti-ribosome IgG. Next, $1\times10^8$ SA magnetic beads were added to capture the Ab-ribosome protein complexes (8000 molecules of antibody per bead). The unbound supernatant was removed from the bead fraction and re-captured ("recapt") using 200 ng biotin, antibody and $1\times10^8$ SA magnetic beads. The collected beads were denatured and subject to Western blot analysis using rabbit anti-ribosome antibody and anti-rabbit Horse Radish Peroxidase (HRP) secondary antibody. The absence of ribosomal proteins in the recapture experiment with lysate where ribosomal proteins had previously been captured, suggests that the first capture step was sufficient in capturing all of the ribosomal proteins.

Example 4

Capture of Ribosomes Using Various Formats of Bead Amplification

Experiments were performed to compare the various assay formats depicted in FIG. 8, panels A-C and F (i.e, Methods 1a, 1b, 2, 3 and 6). Essentially, *E. coli* lysates (500,000 cells) were prepared by lysing bacterial cells in 6M (10,000 cells/µl) guanidine thiocyanate. The guanidine thiocyanate concentration was then reduced to 0.12 or 0.6 M by dilution into phosphate buffer (e.g., dilution of 90,000 cells into 450 µl). Ribosomes were then captured using one of the ribosome capture detection methods shown in FIG. 8 (Table 1).

| Method | Number of *E. coli* cells | Signal over 0 cell control |
|---|---|---|
| Method 1a | 10,000 | 6.05 |
|  | 10,000 | 13.87 |
|  | 20,000 | 15.22 |
|  | 20,000 | 119.85 |
| Method 1b | 20,000 | 4.02 |
| Method 2 | 10,000 | 2.33 |
|  | 10,000 | 1.72 |
|  | 20,000 | 1.85 |
|  | 20,000 | 30.00 |
| Method 3 | 2,000 | 6.17 |
|  | 10,000 | 3.16 |
| Method 6 (1)* | 4,000 | 9.3 |
| Method 6 (2) | 500 | 1.8 |
|  | 2,000 | 2.2 |

*Experiments 1 and 2.

Additional experiments were performed using the method depicted in panel 8F. This method utilizes addition of the bead-Ab2 (carboxy beads and rabbit anti-ribosome antibodies) to the lysate. This allows the ribosomes to bind to the bead, similar to a regular sandwich ELISA where the 'capture' antibodies are immobilized on a surface. The Ab1-biotin (guinea pig) was then added directly to the mixture without any wash steps. The bead-Ab2-ribosome-Ab1 complexes are captured using streptavidin (SA) beads and are detected using secondary antibodies to Ab2. It was found that this approach worked when rabbit Ab-carboxy beads (Ab2-bead) and biotin, guinea pig antibodies (Ab1) were used.

Thus, in this experiment, lysate from 2,500, 5,000, 10,000, or 20,000 cells were incubated with about $1.3 \times 10^8$ carboxy beads (0.1 μm) with rabbit anti-ribosome antibody (anti-ribo Ab). 10 ng ($4 \times 10^{10}$ IgG molecules) biotinylated guinea pig, anti-ribo antibodies were then added and incubated further. The bead-Ab-ribo protein-Ab complexes were captured with about $4 \times 10^7$ Cl SA Dynabeads. Detection was performed with 10 ng anti-rabbit antibody labeled with horse radish peroxidase (HRP). One-fifth of the sample was loaded onto a microplate for detection with Sirius HRP substrate in a luminometer. It can be seen that the signal was detected for as little as 500 cells.

Example 5

Lateral Flow Assay

A LFA test strip was developed in collaboration with Medtox (A LabCorp company). The strip consists of a nitrocellulose membrane and an absorbent pad in contact with the nitrocellulose membrane. The nitrocellulose membrane contains a test line with rabbit, anti-ribosome antibodies, and a control line with goat anti-rabbit antibodies. A schematic of the strip is shown in FIG. 10A.

The assay was performed by applying the sample (0-10 ng ribosomal protein) to the bottom of the strip ("sample application region") and allowing the sample to flow by capillary action across the nitrocellulose surface. Ribosomes present in the sample bind to the immobilized anti-ribosome antibodies at the test line, while the rest of the material in the sample continue into the absorbent pad. The strips were then incubated with a carbon black nanostring (CBNS) that was pre-coated with rabbit anti-ribosome antibodies (CBNS-Ab) and the CBNS-Ab complex allowed to move by capillary action in the same direction as the sample across the nitrocellulose surface. Essentially, antibody coating onto CBNS is done by incubating a solution of antibodies with a CBNS solution containing between 5-25 mM NaCl. Antibody binding to CBNS is non-specific. After an hour incubation, CBNS-Ab complexes are washed and passivated using bovine serum albumin. The CBNS-Ab complexes that interacted with ribosomes bound to the test line resulted in a gray to black line, whereas any unbound CBNS-Ab continued up the strip and was bound to the anti-rabbit control line, which resulting in a gray/black line at that position of the strip. If the sample does not contain ribosomal proteins, no line will form at the test line but will form a line at the control line.

An example experiment is shown in FIGS. 10C and 10D. The experiment shown in panel C shows the use of a single rabbit anti-ribosome antibody CBNS used for detection of ribosomes. In this experiment, purified *E. coli* ribosomes (10 or 100 ng) were run on LFA strips in LFA running buffer (25 mM Tricine, 5% Maltitol, 2% Sodium Saccharine, 0.025% polyvinylpyrrolidone, 0.05% Poly(vinyl alcohol), 0.5% Tetronic 1307, 0.5% Tetronic 904 and 0.005% Sodium Azide, pH 8.0). Once all of the sample had entered the strip, CBNS with rabbit anti-ribosome antibodies were loaded onto the strips. The strips were then imaged and line intensity quantified using ImageJ software (NIH).

The experiment shown in panel D uses two different CBNS complexes. One has biotin anti-ribosome antibody (CBNS-Ab) and the second complex has streptavidin-horse radish peroxidase (CBNS-SA-HRP). In this experiment, purified *E. coli* ribosomes (5 ng) were run on LFA strips in LFA running buffer. Once all of the sample had entered the strip, CBNS with biotinylated, rabbit anti-ribosome antibodies were loaded onto the strips (CNBS-Ab (FIG. 10D upper four strips). To half of the samples, the secondary CBNS with SA-HRP was loaded onto the strips. The SA moiety on this secondary CBNS is able to bind the biotin moiety on the rabbit antibody present on the primary CBNS. This results in an increased amount of total CBNS localized on the test line. Then, HRP substrate (TMB) was added directly to the nitrocellulose surface, and incubated at room temperature for 5 minutes to allow for development of the colored TMB product (FIG. 10D, lower four strips; +TMB (HRP substrate). The strips were then imaged and line intensity quantified using ImageJ software (NIH).

Example 6

Preparation of Biotinylated T4 Bacteriophage

About $2.4 \times 10^{10}$ plaque forming units (PFU) of T4 phage were diluted into 50 μl phosphage buffered saline (PBS). If the phage is in Tris containing buffer, such as TMS, it is necessary to do a buffer transfer as for example, using Zeba Spin columns (Thermo Scientific Pierce, Waltham, Mass.).

To prepare the biotin reagent, 4 mg of Pierce NHS-biotin reagent was added to 1 ml water (4 μg/μl). The reagent was then further diluted to a concentration of 49.4 ng/μl (e.g., add 2 μl to 160.1 μl PBS). Next about 500 ng biotin reagent (10 μl) was added to a tube containing about $2.4 \times 10^{10}$ PFU phage, and allowed to incubate for 2 hours at 4 degrees Celsius (° C.). The biotinylated phage was then desalted using a Zeba column. To desalt the phage, the column was washed 3 times with 300 μl PBS at 1500 g for 1 minute. Next, PBS is added to the phage to bring the total volume to 100 μl, and the phage (100 μl) is added to the Zeba column and centrifuged for 2 min at 1500 g. The phage was then titered using a plaque assay and stored at 4° C.

Example 7

Phage Based Cell Capture and Detection Using Indicator Phage or Indicator Bacteria a. Indicator Bacteria The use of indicator bacteria to assay progeny phage is depicted in FIG. 11. Thus, in this assay, parental phage used to infect a bacterial sample of interest are separated from progeny phage, and then the progeny phage are used to infect indicator bacteria engineered to express a biomolecule that provides a detectable signal upon lysis of the bacteria. For example, bacteria may be engineered to express luciferase protein.

In these experiments, indicator cells were produced using wild type *E. coli* originally obtained from the ATCC, transformed with luciferase plasmids. The luciferase plasmids were based on pGL.4.10 (Firefly luciferase) and pGL.470 (Renilla luciferase) (Promega, Madison, Wis.). Modifications to the plasmids for use in indicator bacteria included inserting a constitutive bacterial promoter ($\sigma^{70}$) upstream of the luciferase gene. This culture (e.g., bacteria expressing luciferase protein) was inoculated at 37° C. with 220 rpm shaking in LB broth with ampicillin (100 μg/ml). In the meantime, about 500 μl of sample bacteria (i.e., the bacteria to be quantified) is loaded onto MilliporeUltrafree MC-HV spin filter in a 2 ml round bottom collection tube, centrifuged at >300 g for 1 minute (up to 8000 rpm in microcentrifuge)

to remove the media and 40 µl biotinylated T4 phage (i.e., about $2.7 \times 10^6$ PFU) phage in LB broth added. The infected bacteria were then washed by applying about 500 µl LB broth and centrifuging at >300 g 1 minute using 2 ml collection tubes 4 times. The filter containing infected bacteria was transferred from the 2 ml collection tube to a fresh 1.5 ml tube, and after the addition of about 200 µl LB broth, the infected bacteria were allowed to incubate 1 hour at 37° C. The infected bacteria were then collected by centrifugation (8000 rpm for 2 minutes) and the filtrate containing progeny phage and any remaining biotinylated parental phage was transferred to streptavidin columns (e.g., GE Healthcare Streptavidin HP SpinTrapcolumns). The columns were then allowed to incubate 20 minutes at room temperature with end-over-end rotation. At this point, the eluate from the column containing progeny phage was transferred to a fresh tube, and the progeny phage collected by centrifugation at 150 g for 1 minute. Progeny phage were detected from this lysate via conventional plaque assay (PFU assay) or subjected to detecting with indicator cells as described below.

Next the indicator cells (i.e., bacteria expressing luciferase) were then diluted to about $10^6$ cells per ml in LB broth, and 10 µl indicator cells added to the progeny phage tube. The phage were allowed to infect the bacteria by adsorption centrifugation (e.g., 8000 rpm for 30 minutes). The infected indicator cells were then resuspended, and incubated with 220 rpm shaking for 37° C. for 1 hour. At this point, the infected indicator cells were isolated using filtration/centrifugation (8,000 rpm for 2 minute) and 10 µA supernatant transferred to a well in a 96 well plate. The level of luciferase was then quantified using a luminometer and the Promega Luciferase assay with 50 µl of Luciferase Assay Substrate.

Data from experiments using this assay are shown in FIGS. 12A-E. FIGS. 12A and 12B demonstrate measurable and comparable signal over background using the phage assay compared to a standard overnight CFU assay. FIG. 12 A shows that as little as 1-2 E. coli cells provide a measurable PFU can be detected (i.e., about 300-460 PFU) of progeny phage via plaque assay. FIG. 12B compares the sensitivity of a standard colony forming unit (CFU) assay to the phage assay of the invention. It can be seen that the phage assay, while much faster to perform, provides about the same sensitivity as compared to the CFU assay, and demonstrates a dose dependent response, with increasing progeny phage arising from increasing sample cells. Though this comprises only the first half of the full phage assay, utilizing plaque assays can gain same day results compared to a standard overnight CFU assay.

FIG. 12C shows detection of phage that are the equivalent of progeny from a single cell (i.e., 100 phage) or 27 cells (i.e., 2700 phage) using Indicator Cells (e.g. second half of the full phage assay), indicator high sensitivity.

FIG. 12D shows the detection of 1, 5 and 7 sample cells (e.g., E. coli), compared to a standard CFU assay (dotted line denotes background level).

FIG. 12E shows the successful detection of 100 to 10,000 bacterial cells (determined microscopically) per sample using the full phage assay (line denotes background level). Thus demonstrating sensitivity from 1 to 10,000 cells with no dilution of the sample. This is 1 or 2 orders of magnitude more sensitive than a standard overnight CFU assay, where more than 500-700 CFU cannot be reliably counted on a Petri dish, in addition to being a much faster assay, performed in approximately 3 hours.

FIG. 12D shows the equivalent of 5 and 500 sample cells (i.e., E. coli) and FIG. 12E shows the detection of 1, 5 and 10 bacterial cells per ml using the progeny phage of FIG. 11. FIG. 12D shows the detection of 1, 5 and 7 sample cells (i.e., E. coli), compared to a standard CFU assay (red line indicator background).

FIG. 12E shows the successful detection of 100 to 10,000 bacterial cells (determined microscopically) per sample using the full phage assay (line indicating background). Thus demonstrating sensitivity from 1 to 10,000 cells with no dilution of the sample. This is 1 or 2 orders of magnitude more sensitive than a standard overnight CFU assay, where more than 500-700 CFU generally cannot be reliably counted on a Petri dish, in addition to being a much faster assay, performed in approximately 3 hours.

b. Indicator Phage

The strategy of using indicator phage is shown in FIG. 13. In this method, the phage capsid protein is fused with luciferase such that progeny phage that are not biotinylated can be separated from parental phage which are biotinylated and directly quantified.

To perform the assay, about 500 µl of sample bacteria (i.e., the bacteria to be quantified) will be loaded onto MilliporeUltrafree MC-HV spin filter in a 2 ml round bottom collection tube, centrifuged at >300 g for 1 minute (up to 8000 rpm in microcentrifuge) to remove the media and 40 µl biotinylated T4 phage (i.e., about $2.7 \times 10^6$ PFU) phage in LB broth added. The infected bacteria will then be washed by applying about 500 µl LB broth and centrifuging at >300 g for 1 minute using 2 ml collection tube 4 times, the filter column containing infected bacteria can then be transferred to fresh tube, and after the addition of about 200 µl LB broth, the infected bacteria will be allowed to incubate 1 hour at 37° C. The infected bacteria will then be collected by centrifugation (8000 rpm for 2 minutes) and the filtrate containing progeny phage and biotinylated parental phage can be transferred to streptavidin columns (e.g., GE Healthcare Streptavidin HP SpinTrapcolumns). The columns will then be allowed to incubate 20 minutes at room temperature with end-over-end rotation. At this point, the eluate from the column containing progeny phage will be transferred to a fresh tube, and the progeny phage collected by centrifugation at 150 g for 1 minute. Next, 10 µl of the flow through will be transferred to a well in a 96 well plate, and the level of luciferase will be quantified using a luminometer and the Promega Luciferase assay with 50 µl Luciferase Assay Reagent.

c. Indicator Phage Soluble Luciferase

The strategy of using indicator phage with soluble luciferase is shown in FIG. 14. In this method, the phage express luciferase instead of Soc capsid protein. Expression of luciferase is driven by the Soc promoter, yielding high expression. In this case there is no need to separate out the parental phage and the progeny phage because parental phage will be free of luciferase (byproduct of phage stock purification). Only a productive infection of bacteria in the sample will yield detectable luciferase.

To perform the assay, about 500 µl of sample bacteria (i.e., the bacteria to be quantified) will be loaded onto MilliporeUltrafree MC-HV spin filter in a 2 ml round bottom collection tube, and centrifuged at >300 g for 1 minute (up to 8000 rpm in microcentrifuge) to remove the media. The spin filter will then be transferred to a fresh tube, about 40 µl biotinylated T4 phage (i.e., about $2.7 \times 10^6$ PFU) phage in LB broth added, and after the addition of about 200 µl LB broth, the infected bacteria will be allowed to incubate 1 hour at 37° C. The infected bacteria will then be collected by centrifugation (8000 rpm for 2 minutes), 10 µl flow through will be transferred to a well in a 96 well plate, and the level of luciferase can be quantified using a luminometer and the Promega Luciferase assay with 50 µl Luciferase Assay Substrate.

The invention is not limited to the exact details shown and described, for variations obvious to one skilled in the art will be included within the invention defined by the claims. While the preferred embodiments of the invention have been illustrated and described, it will be appreciated that various changes can be made therein without departing from the spirit and scope of the invention. All printed patents and publications referred to in this application are hereby incorporated herein in their entirety by this reference.

That which is claimed is:

1. A method for detecting a bacterium of interest comprising the steps of:
    isolating at least one bacterium from other components in a sample;
    infecting the at least one bacterium with a plurality of a lytic parental bacteriophage genetically engineered to express a soluble protein during replication,
    wherein the parental bacteriophage are present in an amount to find, bind, and infect the at least one bacterium in the sample to cause a lytic infection cycle to produce 100 or more progeny phage particles in about one-half hour to one hour
    incubating the at least one infected bacterium;
    lysing the at least one infected bacterium to release the contents in the bacterium;
    detecting the soluble protein expressed during replication of the bacteriophage,
    wherein expression of the soluble protein is driven by a bacteriophage capsid promoter and the soluble protein is not a fusion protein and is not incorporated into the bacteriophage structure,
    wherein detection of the soluble protein indicates that the bacterium is present in the sample,
    and
    wherein the method detects as little as a single bacterium in the sample.

2. The method of claim 1, further comprising washing the infected bacterium before the incubating step to remove unadsorbed parental bacteriophage.

3. The method of claim 1, wherein the soluble protein is selected from the group consisting of an enzyme that may be used to convert a substrate to a visible product, a fluorophore, and a luminescent molecule.

4. The method of claim 3, wherein the soluble protein is luciferase.

5. A method for detecting a bacterium of interest comprising the steps of:
    isolating at least one bacterium from other components in a sample;
    infecting the at least one bacterium with a plurality of a genetically unmodified lytic parental bacteriophage,
    wherein the parental bacteriophage are present in an amount to find, bind, and infect the at least one bacterium in the sample to cause a lytic infection cycle to produce 100 or more progeny phage particles in about one-half hour to one hour, and wherein unadsorbed parental bacteriophage are removed from the sample by washing through a filter;
    incubating until the at least one infected bacterium is lysed to release progeny bacteriophage present in the bacterium;
    infecting indicator bacteria with the progeny bacteriophage, wherein the indicator bacteria comprise a plasmid having a genetic sequence that encodes a detectable protein that is released upon lysis of the indicator bacteria, and wherein the plasmid further includes a constitutive bacterial promoter upstream of the genetic sequence that encodes the detectable protein; and
    detecting the detectable protein,
    wherein detection of the detectable protein indicates that the bacterium is present in the sample,
    and
    wherein the method detects as little as a single bacterium in the sample.

6. The method of claim 5, further comprising separating the parental bacteriophage from the progeny bacteriophage after the incubating step and before the progeny bacteriophage are used to infect the indicator bacteria.

7. The method of claim 5, wherein the detectable protein comprises luciferase.

8. A kit comprising components for detecting a bacterium of interest comprising:
    a component for isolating at least one bacterium of interest from other components in a sample, wherein the component comprises a bacteriological filter;
    a composition comprising a lytic bacteriophage genetically engineered to express a soluble protein during replication, wherein the soluble protein is not a fusion protein and is not incorporated into the bacteriophage structure and wherein expression of the soluble protein is driven by a bacteriophage capsid promoter; and
    a component for detecting the soluble protein expressed during replication of the bacteriophage.

9. The method of claim 6, wherein the parental bacteriophage are biotinylated, and wherein the separating comprises collecting lysate from the infected and incubated sample bacteria by spin filtering, and then transferring filtrate containing the progeny bacteriophage and any remaining biotinylated parental bacteriophage to a support comprising streptavidin to separate any remaining biotinylated parental bacteriophage from the progeny bacteriophage.

10. The method of claim 5, wherein the method is performed in approximately 3 hours.

11. The method of claim 2, wherein the detecting step is performed without separating the remaining parental bacteriophage from the progeny bacteriophage.

12. The kit of claim 8, further comprising a component for removing unadsorbed parental bacteriophage after infecting and before lysis of the at least one bacterium in the sample.

13. The method of claim 1, wherein the isolating comprises concentrating the sample about 1000-fold.

14. The method of claim 1, wherein the isolating comprises filtering the sample through a bacteriological spin filter.

15. The method of claim 14, wherein all steps of the method are performed using the bacteriological spin filter.

16. The method of claim 1, wherein the incubating is for an hour or less.

17. The method of claim 5, wherein the isolating comprises concentrating the sample about 1000-fold.

* * * * *